(12) United States Patent
He et al.

(10) Patent No.: US 12,227,613 B2
(45) Date of Patent: Feb. 18, 2025

(54) PHOTO-PATTERNABLE ORGANIC SEMICONDUCTOR (OSC) POLYMERS AND METHODS OF FORMATION AND APPLICATIONS THEREOF

(71) Applicant: Corning Incorporated, Corning, NY (US)

(72) Inventors: Mingqian He, Horseheads, NY (US); Xin Li, Shanghai (CN); Yang Li, Shanghai (CN); Hongxiang Wang, Shanghai (CN)

(73) Assignee: CORNING INCORPORATED, Corning, NY (US)

( * ) Notice: Subject to any disclaimer, the term of this patent is extended or adjusted under 35 U.S.C. 154(b) by 511 days.

(21) Appl. No.: 17/495,970

(22) Filed: Oct. 7, 2021

(65) Prior Publication Data
US 2022/0119591 A1 Apr. 21, 2022

(30) Foreign Application Priority Data
Oct. 16, 2020 (CN) .......................... 202011108416.7

(51) Int. Cl.
C08G 61/12 (2006.01)
C09D 5/24 (2006.01)
(Continued)

(52) U.S. Cl.
CPC ............. *C08G 61/126* (2013.01); *C09D 5/24* (2013.01); *C09D 165/00* (2013.01);
(Continued)

(58) Field of Classification Search
None
See application file for complete search history.

(56) References Cited

U.S. PATENT DOCUMENTS

| 8,846,855 | B2 * | 9/2014 | He | C08G 61/126 |
| | | | | 528/370 |
| 8,912,305 | B2 * | 12/2014 | Duggeli | C08G 61/12 |
| | | | | 528/367 |

(Continued)

FOREIGN PATENT DOCUMENTS

| CN | 109575244 | A | * | 4/2019 |
| WO | 2008/013427 | A1 | | 1/2008 |

OTHER PUBLICATIONS

Yang et al (Patternable Conjugated Polymers with Latent Hydrogen-Bonding on the Main Chain; Kun Yang, Tianda He, Xiaoyi Chen, Stephen Z. D. Cheng, and Yu Zhu; Macromolecules 2014 47 (24), 8479-8486). (Year: 2014).*

(Continued)

*Primary Examiner* — Sean M DeGuire
*Assistant Examiner* — Andrew Preston Traywick
(74) *Attorney, Agent, or Firm* — Travis B. Gasa

(57) ABSTRACT

A method, includes: reacting at least one donor group with at least one protected acceptor group to form a plurality of protecting group-containing OSC polymers; removing the protecting group from the plurality of protecting group-containing OSC polymers to form H-bonding sites; and fusing the H-bonding sites of a first OSC polymer backbone with H-bonding sites of a second OSC polymer backbone to form π-π interactions between conjugated OSC polymers.

19 Claims, 9 Drawing Sheets

(51) Int. Cl.

| | |
|---|---|
| *C09D 165/00* | (2006.01) |
| *G01N 33/00* | (2006.01) |
| *G03F 7/038* | (2006.01) |
| *G03F 7/039* | (2006.01) |
| *H10K 10/46* | (2023.01) |
| *H10K 85/10* | (2023.01) |

(52) U.S. Cl.
CPC ..... *G01N 33/0036* (2013.01); *G01N 33/0037* (2013.01); *G01N 33/0054* (2013.01); *G03F 7/038* (2013.01); *G03F 7/039* (2013.01); *H10K 10/466* (2023.02); *H10K 10/488* (2023.02); *H10K 85/113* (2023.02); *H10K 85/151* (2023.02); *C08G 2261/124* (2013.01); *C08G 2261/1412* (2013.01); *C08G 2261/18* (2013.01); *C08G 2261/228* (2013.01); *C08G 2261/3223* (2013.01); *C08G 2261/3241* (2013.01); *C08G 2261/3243* (2013.01); *C08G 2261/41* (2013.01); *C08G 2261/80* (2013.01); *C08G 2261/92* (2013.01); *C08G 2261/94* (2013.01)

(56) References Cited

U.S. PATENT DOCUMENTS

| | | | |
|---|---|---|---|
| 2013/0109821 A1* | 5/2013 | He | H10K 85/151 526/256 |
| 2017/0331043 A1 | 11/2017 | Kuhn et al. | |
| 2018/0052136 A1* | 2/2018 | Diao | H10K 71/20 |
| 2018/0244893 A1 | 8/2018 | Kuhn et al. | |
| 2021/0341838 A1 | 11/2021 | Deng et al. | |

OTHER PUBLICATIONS

Matthews et al (James R. Matthews, Weijun Niu, Adama Tandia, Arthur L. Wallace, Jieyu Hu, Wen-Ya Lee, Gaurav Giri, Stefan C. B. Mannsfeld, Yingtao Xie, Shucheng Cai, Hon Hang Fong, Zhenan Bao, and Mingqian He; Chemistry of Materials 2013 25 (5), 782-789) (Year: 2013).*
Translated Description of Cai et al (Year: 2013).*
Choi, M.S., et al., "Colorimetric Anion Sensing and Color Imaging Based on Catalyzed Deprotection in a New Azonaphthol Chromophore", Journal of Nanoscience and Nanotechnology, vol. 6(11), Nov. 2006 pp. 3551-3554.
Choi, M.S., et al., "New conjugated polymers comprising ortho-phenylazonaphthols: Synthesis and chromogenic behaviors", Journal of Polymer Science Part A: Polymer Chemistry, vol. 45(19), Oct. 2007, pp. 4430-4440.
Del Campo, A., et al., "Surface modification with orthogonal photosensitive silanes for sequential chemical lithography and site-selective particle deposition", Angew Chem Int Ed Engl, vol. 44(50), Jul. 2005, pp. 4707-4712.
Dependence of Band Offset and Open-Circuit Voltage on the Interfacial Interaction between TiO2 and Carboxylated Polythiophenes. J. Phys. Chem. B, vol. 110, Jan. 2006, pp. 3257-3261.
Glowacki, E.D., et al., "A facile protection-deprotection route for obtaining indigo pigments as thin films and their applications in organic bulk heterojunctions", Chem Commun (Camb), vol. 49(54), 2013, pp. 6063-6065.
Gumbley, P., et al., "Wavelength-Selective Disruption and Triggered Release with Photolabile Polyelectrolyte Multilayers", Chemistry of Materials, vol. 26(3), Jan. 2014, pp. 1450-1456.
Guo, Z.-H., et al., "A side-chain engineering approach to solvent-resistant semiconducting polymer thin films", Polymer Chemistry, vol. 7(3), 2016, pp. 648-655.
Huang, Q., et al., "Photocleavable coumarin crosslinkers based polystyrene microgels: phototriggered swelling and release", Journal of Materials Chemistry, vol. 22(35), 2012, 8 pages.

Jakob, S., et al., "Synthesis of Polyphenylenes from a Soluble Precursor: The "Shaving" Approach", Macromolecules, vol. 43(19), Oct. 2010, pp. 7916-7918.
Jianfei Y, et al, "Synthesis, Solid-Phase Reaction, and Patterning of Acid-Labile 3,4-Ethylenedioxythiophene-Based Conjugated Polymers", Chem. Mater., vol. 14, Aug. 2002, pp. 3705-3714.
Jiang, J., et al., "Photoinduced morphology switching of polymer nanoaggregates in aqueous solution", Langmuir, vol. 26(17), Sep. 2010, pp. 14247-14254.
Jinsong Liu, et al, "Polythiophene Containing Thermally Removable Solubilizing Groups Enhances the Interface and the Performance of Polymer-Titania Hybrid Solar Cells", J. Am. Chem. Soc., vol. 126, 2004, pp. 9486-9487.
Johnson, R.S., et al., "Conjugated polymer patterning through photooxidative backbone cleavage", Macromol Rapid Commun, vol. 35(12), Apr. 2014, pp. 1116-1120.
Johnson, R.S., et al., "Photopatterning poly(p-phenylenevinylene) from xanthate precursor polymers", Chem Commun (Camb), vol. 47(13), Feb. 2011, pp. 3936-3938.
Klauk, H., "Organic thin-film transistors", Chemical Society Reviews, vol. 39(7), Apr. 2010, pp. 2643-2666.
Krebs, F.C. et al, "Using light-induced thermocleavage in a roll-to-roll process for polymer solar cells", ACS Appl Mater Interfaces, vol. 2(3), Mar. 2010, pp. 877-887.
Krebs, F.C., et al, "A self-calibrating led-based solar test platform", Progress in Photovoltaics: Research and Applications, vol. 19(1), 2011, pp. 97-112.
Kumar, B. et al., "Organic Thin Film Transistors: Structures, Models, Materials, Fabrication, and Applications", A Review. Polymer Reviews, vol. 54(1), Feb. 2014, pp. 81.
Kun Yang, et al., "Patternable Conjugated Polymers with Latent Hydrogen-Bonding on the Main Chain", Macromolecules, 47, Dec. 2014, pp. 8.
Latent pigments activated by heat. Nature, vol. 388, Jul. 1997. 388: pp. 2.
Lee, S.K., et al., "Photolithographic Micropatterning of an Electroluminescent Polymer Using Photobase Generator", Macromolecules, vol. 36(24), Nov. 2003, pp. 9252-9256.
Liu, C., et al., "Donor-Acceptor Copolymers Based on Thermally Cleavable Indigo, Isoindigo, and DPP Units: Synthesis, Field Effect Transistors, and Polymer Solar Cells", ACS Appl Mater Interfaces, vol. 7(17), 2015, pp. 9038-9051.
Liu, C., et al., "Synthesis of Anthracene-Based Donor-Acceptor Copolymers with a Thermally Removable Group for Polymer Solar Cells", Macromolecules, vol. 47(24), Dec. 2014, pp. 8585-8593.
Nielsen, C.B., et al., "Improved field-effect transistor performance of a benzotrithiophene polymer through ketal cleavage in the solid state", ACS Appl Mater Interfaces, vol. 5(5), 2013, pp. 1806-1810.
Petra Stegmaier, et al, "Photoresponsive Surfaces with Two Independent Wavelength-Selective Functional Levels", Langmuir, vol. 24, Sep. 2008, pp. 11872-11879.
Reese et al., "Organic Thin Film Transistors", Materials Today, vol. 7, No. 9, Sep. 2004, pp. 20-27.
Shaker, M., et al., "Isoindigo/DPP-based polymers containing a thermolabile group", RSC Advances, vol. 7(27), pp. 16302-16310.
Smith, Z.C., et al, "Photoinduced Aggregation of Polythiophenes", ACS Macro Letters, vol. 1(7), Jun. 2012, pp. 825-829.
Smith, Z.C., et al., "Thiophene-Based Conjugated Polymers with Photolabile Solubilizing Side Chains", Macromolecules, vol. 48(4), Feb. 2015, pp. 959-966.
Søndergaard, R.R., et al, "Low-temperature side-chain cleavage and decarboxylation of polythiophene esters by acid catalysis", Journal of Polymer Science Part A: Polymer Chemistry, vol. 50(6), Mar. 2012, pp. 1127-1132.
Su, G.M., et al., "Polymer Side Chain Modification Alters Phase Separation in Ferroelectric-Semiconductor Polymer Blends for Organic Memory", ACS Macro Letters, vol. 3(12), pp. 1244-1248.
Sun, B., et al., "Diketopyrrolopyrrole-based semiconducting polymer bearing thermocleavable side chains", Journal of Materials Chemistry, vol. 22(36), Jul. 2012, pp. 18950.
Sun, J., et al, "Materials for Printable, Transparent, and Low-Voltage Transistors", Advanced Functional Materials, vol. 21(1), 2011, pp. 29-45.

(56) References Cited

OTHER PUBLICATIONS

Sytnyk, M., et al., "Hydrogen-bonded organic semiconductor micro- and nanocrystals: from colloidal syntheses to (opto-)electronic devices", J Am Chem Soc, vol. 136(47), 2014, pp. 16522-16532.

Thomas, S.W., "New Applications of Photolabile Nitrobenzyl Groups in Polymers", Macromolecular Chemistry and Physics, vol. 213(23), Oct. 2012, pp. 2443-2449.

Uemura, T., et al., "Synthesis of Semiconducting Polymers through Soluble Precursor Polymers with Thermally Removable Groups and Their Application to Organic Transistors", ACS Macro Letters, vol. 2(9), Sep. 2013, pp. 830-833.

Uh, K., et al., "A Precursor Approach to Electrospun Polyaniline Nanofibers for Gas Sensors", Macromolecular Materials and Engineering, vol. 301(11), 2016, pp. 1320-1326.

Yang, K., et al., "Patternable Conjugated Polymers with N-Boc group by PAG", Macromolecules, vol. 47(24), 2014, pp. 8479-8486.

Yang, Y., et al., "Highly Sensitive Thin-Film Field-Effect Transistor Sensor for Ammonia with the DPP-Bithiophene Conjugated Polymer Entailing Thermally Cleavable tert-Butoxy Groups in the Side Chains", ACS Appl Mater Interfaces, vol. 8(6), 2016, pp. 3635-3643.

Zhang, H., et al., "1,4-Diketo-pyrrolo[3,4-c]pyrroles (DPPs) based insoluble polymer films with lactam hydrogens as renewable fluoride anion chemosensor", Polymer, vol. 149, 2018, pp. 266-272.

Zhao, H., et al., "o-Nitrobenzyl Alcohol Derivatives: Opportunities in Polymer and Materials Science", Macromolecules, vol. 45(4), Jan. 2012, pp. 1723-1736.

Zou, Y., et al., "Synthesis and Solution Processing of a Hydrogen-Bonded Ladder Polymer", Chem, vol. 2(1), 2017, pp. 139-152.

* cited by examiner

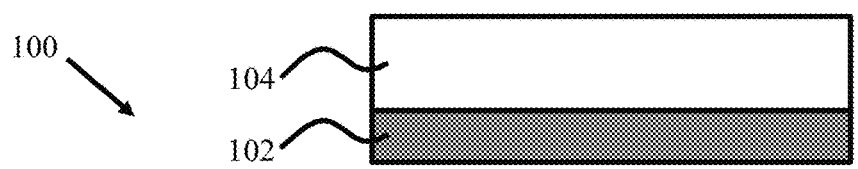
FIG. 1A
FIG. 1B
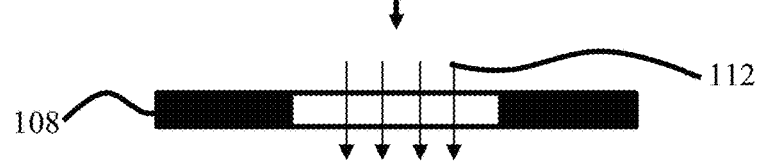
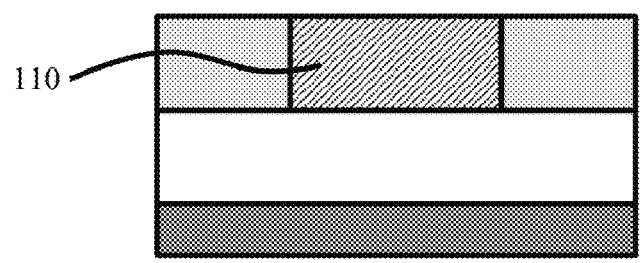
FIG. 1C
FIG. 1D
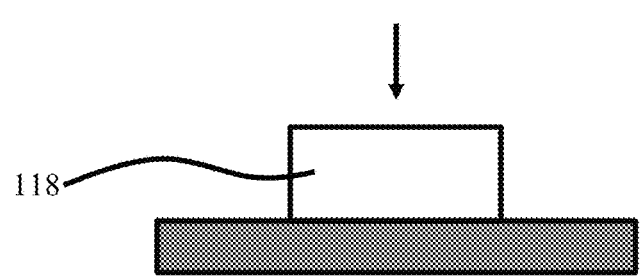
FIG. 1E

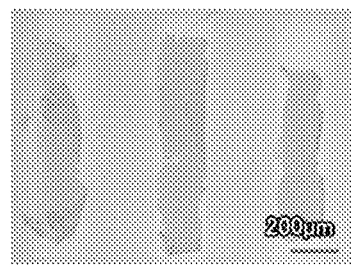 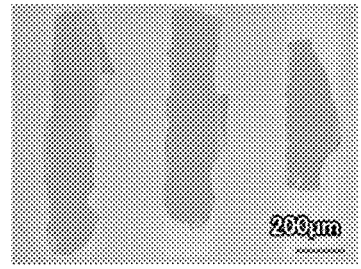
FIG. 9A					FIG. 9B
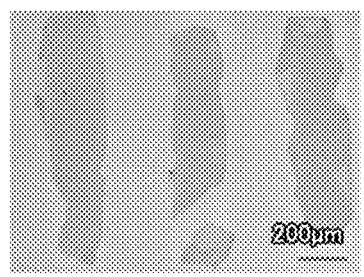 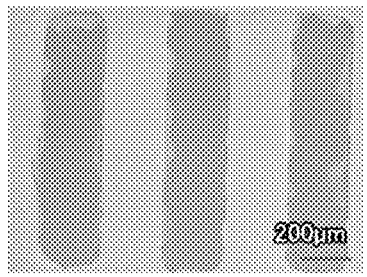
FIG. 9C					FIG. 9D

PHOTO-PATTERNABLE ORGANIC SEMICONDUCTOR (OSC) POLYMERS AND METHODS OF FORMATION AND APPLICATIONS THEREOF

CROSS REFERENCE TO RELATED APPLICATIONS

This application claims the benefit of priority under 35 U.S.C. § 119 of Chinese Patent Application Serial No. 202011108416.7, filed on Oct. 16, 2020, the content of which is relied upon and incorporated herein by reference in its entirety.

BACKGROUND

1. Field

This disclosure relates to photo-patternable organic semiconductor (OSC) polymers as semiconducting layers for organic thin-film transistor (OTFT)-based electronic devices and sensors.

2. Technical Background

Organic thin-film transistors (OTFTs) have garnered extensive attention as alternatives to conventional silicon-based technologies, which require high temperature and high vacuum deposition processes, as well as complex photolithographic patterning methods. Semiconducting (i.e., organic semiconductor, OSC) layers are one important component of OTFTs which can effectively influence the performance of devices.

Traditional technologies in the manufacture of inorganic TFT device arrays often rely on photolithography as the patterning process. However, photolithography usually involves harsh oxygen ($O_2$) plasma during pattern transfer or photoresist removal and aggressive developing solvents which may severely damage the OSC layer and lead to significant deterioration of device performance.

This disclosure presents improved photo-patternable organic semiconductor polymers and use thereof for OSC layers of organic thin-film transistors.

SUMMARY

In some embodiments, a method comprises: reacting at least one donor group with at least one protected acceptor group to form a plurality of protecting group-containing OSC polymers; removing the protecting group from the plurality of protecting group-containing OSC polymers to form H-bonding sites; and fusing the H-bonding sites of a first OSC polymer backbone with H-bonding sites of a second OSC polymer backbone to form π-π interactions between conjugated OSC polymers.

In one aspect, which is combinable with any of the other aspects or embodiments, the step of removing is conducted by thermal annealing, UV irradiation, or a combination thereof.

In one aspect, which is combinable with any of the other aspects or embodiments, the at least one donor group is tetrathienoacene (FT4). In one aspect, which is combinable with any of the other aspects or embodiments, the at least one donor group is selected from at least one of the compounds in Scheme 4.

In one aspect, which is combinable with any of the other aspects or embodiments, the at least one protected acceptor group is selected from at least one of: diketopyrrolopyrrole (DPP), indigo, isoindigo, or combinations thereof. In one aspect, which is combinable with any of the other aspects or embodiments, the at least one protected acceptor group is selected from at least one of the compounds in Scheme 2.

In one aspect, which is combinable with any of the other aspects or embodiments, the protecting group is selected from at least one of: tert-butoxycarbonyl (t-Boc), nitrobenzyl ester (NBE), ortho-nitrobenzyl (ONB), esters, ethers, xanthane, tetrahydropyranyl (THP), silyls, ketones, ketals, halogens, benzoins, coumarins, benzoquinolone, benzocoumarin, 7-nitroindoline, p-hydroxyphenacyl, or combinations thereof.

In one aspect, which is combinable with any of the other aspects or embodiments, the step of reacting comprises: reacting at least one donor group with at least one protected acceptor group and at least one non-protected acceptor group to form a plurality of protecting group-containing crossbred OSC polymers. In one aspect, which is combinable with any of the other aspects or embodiments, the at least one non-protected acceptor group is selected from at least one of: diketopyrrolopyrrole (DPP), indigo, isoindigo, or combinations thereof. In one aspect, which is combinable with any of the other aspects or embodiments, the at least one non-protected acceptor group is selected from at least one of the compounds in Scheme 2.

In one aspect, which is combinable with any of the other aspects or embodiments, the step of removing the protecting group comprises: dissolving the plurality of protecting group-containing OSC polymers in a solvent to form a mixture; and disposing the mixture onto a substrate to form a film. In one aspect, which is combinable with any of the other aspects or embodiments, the step of removing the protecting group further comprises: thermal annealing the film at a temperature in a range of 100° C. to 500° C. In one aspect, which is combinable with any of the other aspects or embodiments, the step of removing the protecting group further comprises: exposing the film to UV light having an energy in a range of 10 mJ/cm$^2$ to 2000 mJ/cm$^2$. In one aspect, which is combinable with any of the other aspects or embodiments, the UV light has an energy in a range of 400 mJ/cm$^2$ to 1600 mJ/cm$^2$.

In some embodiments, an electronic device comprises conjugated OSC polymers and configured to sense nitrogen-based gas at a detection level of 10 parts-per-billion (ppb). In one aspect, which is combinable with any of the other aspects or embodiments, the nitrogen-based gas comprises at least one of: ammonia ($NH_3$), nitric oxide (NO), triethylamine ($Et_3N$), piperidine (($CH_2$)$_5$NH), 1,4-diaminobutane ($NH_2(CH_2)_4NH_2$), or combinations thereof. In some embodiments, an electronic device comprises conjugated OSC polymers and configured to sense gas, wherein the gas comprises at least one of: acetone, carbon monoxide (CO), hydrogen sulfide ($H_2S$), dichloromethane ($CH_2Cl_2$), ethanol ($CH_3CH_2OH$), ethyl acetate ($C_4H_8O_2$), hexane, hydrogen chloride (HCl), or combinations thereof.

BRIEF DESCRIPTION OF THE DRAWINGS

The disclosure will become more fully understood from the following detailed description, taken in conjunction with the accompanying figures, in which:

FIGS. 1A to 1E illustrate traditional patterning techniques of organic semiconductor materials utilizing photoresists.

FIGS. 9A to 9D illustrate ultraviolet (UV)-patterned images of t-Boc OSC polymers exposed to various light energies, according to some embodiments.

DETAILED DESCRIPTION

Figure 2A:
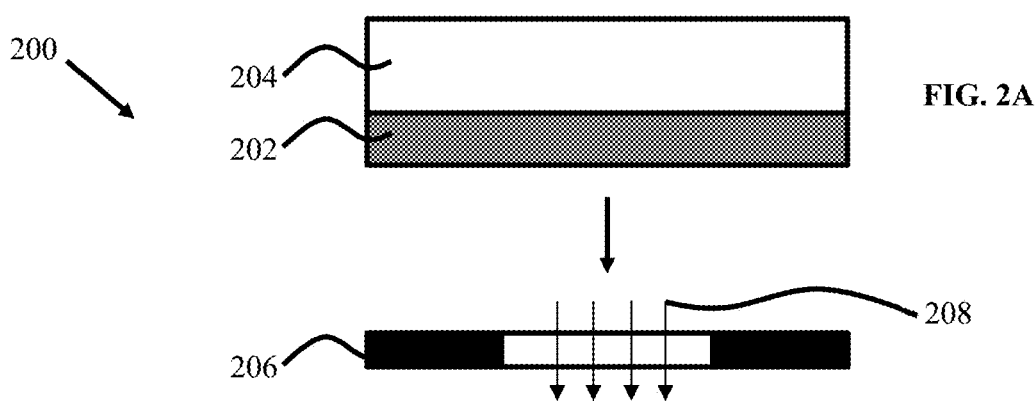
FIGS. 2A to 2C illustrate patterning techniques of organic semiconductor materials, according to some embodiments.

Reference will now be made in detail to exemplary embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments. It should be understood that the present application is not limited to the details or methodology set forth in the description or illustrated in the figures. It should also be understood that the terminology is for the purpose of description only and should not be regarded as limiting.

Additionally, any examples set forth in this specification are illustrative, but not limiting, and merely set forth some of the many possible embodiments of the claimed invention. Other suitable modifications and adaptations of the variety of conditions and parameters normally encountered in the field, and which would be apparent to those skilled in the art, are within the spirit and scope of the disclosure.

Definitions

The term 'cinnamate' refers to a salt or ester of cinnamic acid, which is an organic compound with the formulate $C_6H_5CH=CHCOOH$. Both cinnamic acids and cinnamates are classified as unsaturated carboxylic acids. Cinnamates may occur as both cis and trans isomers.

The term 'chalcone' refers to an aromatic ketone and an enone that forms the central core for a variety of important biological compounds, collectively as chalcones or chalconoids. Examples of chalcones include benzylideneacetophenone, phenyl styryl ketone, benzalacetophenone, β-phenylacrylophenone, γ-oxo-α,γ-diphenyl-α-propylene, and α-phenyl-β-benzoylethylene.

The term 'coumarin' (i.e., 2H-chromen-2-one) refers to an aromatic organic chemical compound with formula $C_9H_6O_2$. It is a benzene molecule with two adjacent hydrogen atoms replaced by a lactone-like chain —O—, forming a second six-membered heterocycle that shares two carbons with the benzene ring. It may be placed in the benzopyrone chemical class and considered as a lactone.

The term 'arylalkene' refers to an alkene group that is directly bonded to an aromatic group.

The term "alkyl group" refers to a monoradical branched or unbranched saturated hydrocarbon chain having 1 to 40 carbon atoms. This term is exemplified by groups such as methyl, ethyl, n-propyl, isopropyl, n-butyl, isobutyl, t-butyl, pentyl, n-hexyl, n-heptyl, n-octyl, n-decyl, or tetradecyl, and the like. The alkyl group can be substituted or unsubstituted.

The term "substituted alkyl group" refers to: (1) an alkyl group as defined above, having 1, 2, 3, 4 or 5 substituents, typically 1 to 3 substituents, selected from the group consisting of alkenyl, alkynyl, alkoxy, aralkyl, aldehyde, cycloalkyl, cycloalkenyl, acyl, acylamino, acyl halide, acyloxy, amino, aminocarbonyl, alkoxycarbonylamino, azido, cyano, halogen, hydroxy, keto, thiocarbonyl, carboxy, carboxyalkyl, arylthiol, ester, heteroarylthio, heterocyclylthio, hydroxyl, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl and —SO$_2$-heteroaryl, thioalkyl, vinyl ether. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —S(O)$_n$R$_{SO}$, where R$_{SO}$ is alkyl, aryl, or heteroaryl and n is 0, 1 or 2; or (2) an alkyl group as defined above that is interrupted by 1-10 atoms independently chosen from oxygen, sulfur and NR$_a$, where R$_a$ is chosen from hydrogen, alkyl, cycloalkyl, alkenyl, cycloalkenyl, alkynyl, aryl, heteroaryl and heterocyclyl. All substituents may be optionally further substituted by alkyl, alkoxy, halogen, $CF_3$, amino, substituted amino, cyano, or —S(O)$_n$R$_{SO}$, in which R$_{SO}$ is alkyl, aryl, or heteroaryl and n is 0, 1 or 2; or (3) an alkyl group as defined above that has both 1, 2, 3, 4 or 5 substituents as defined above and is also interrupted by 1-10 atoms as defined above. For example, the alkyl groups can be an alkyl hydroxy group, where any of the hydrogen atoms of the alkyl group are substituted with a hydroxyl group.

The term "alkyl group" as defined herein also includes cycloalkyl groups. The term "cycloalkyl group" as used herein is a non-aromatic carbon-based ring (i.e., carbocyclic) composed of at least three carbon atoms, and in some embodiments from three to 20 carbon atoms, having a single cyclic ring or multiple condensed rings. Examples of single ring cycloalkyl groups include, but are not limited to, cyclopropyl, cyclobutyl, cyclopentyl, cyclohexyl, cyclooctyl, and the like. Examples of multiple ring cycloalkyl groups include, but are not limited to, adamantanyl, bicyclo[2.2.1]heptane, 1,3,3-trimethylbicyclo[2.2.1]hept-2-yl, (2,3,3-trimethylbicyclo[2.2.1]hept-2-yl), or carbocyclic groups to which is fused an aryl group, for example indane, and the like. The term cycloalkyl group also includes a heterocycloalkyl group, where at least one of the carbon atoms of the ring is substituted with a heteroatom such as, but not limited to, nitrogen, oxygen, sulfur, or phosphorus.

The term "unsubstituted alkyl group" is defined herein as an alkyl group composed of just carbon and hydrogen.

The term "acyl" denotes a group —C(O)R$_{CO}$, in which R$_{CO}$ is hydrogen, optionally substituted alkyl, optionally substituted cycloalkyl, optionally substituted heterocyclyl, optionally substituted aryl, and optionally substituted heteroaryl.

The term "aryl group" as used herein is any carbon-based aromatic group (i.e., aromatic carbocyclic) such as having a single ring (e.g., phenyl) or multiple rings (e.g., biphenyl), or multiple condensed (fused) rings (e.g., naphthyl or anthryl). These may include, but are not limited to, benzene, naphthalene, phenyl, etc.

The term "aryl group" also includes "heteroaryl group," meaning a radical derived from an aromatic cyclic group (i.e., fully unsaturated) having 1, 2, 3, 4, 5, 6, 7, 8, 9, 10, 11, 12, 13, 14, or 15 carbon atoms and 1, 2, 3 or 4 heteroatoms selected from oxygen, nitrogen, sulfur, and phosphorus within at least one ring. In other words, heteroaryl groups are aromatic rings composed of at least three carbon atoms that has at least one heteroatom incorporated within the ring of the aromatic group. Such heteroaryl groups can have a single ring (e.g., pyridyl or furyl) or multiple condensed rings (e.g., indolizinyl, benzothiazolyl, or benzothienyl). Examples of heteroaryls include, but are not limited to, [1,2,4]oxadiazole, [1,3,4]oxadiazole, [1,2,4]thiadiazole, [1,3,4]thiadiazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, triazole, oxazole, thiazole, naphthyridine, and the like as well as N-oxide and N-alkoxy derivatives of nitrogen containing heteroaryl compounds, for example pyridine-N-oxide derivatives.

Unless otherwise constrained by the definition for the heteroaryl substituent, such heteroaryl groups can be optionally substituted with 1 to 5 substituents, typically 1 to 3 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The aryl group can be substituted or unsubstituted. Unless otherwise constrained by the definition for the aryl substituent, such aryl groups can optionally be substituted with from 1 to 5 substituents, typically 1 to 3 substituents, selected from the group consisting of alkyl, alkenyl, alkynyl, alkoxy, aldehyde, cycloalkyl, cycloalkenyl, acyl, acylamino, acyloxy, amino, aminocarbonyl, alkoxycarbonylamino, azido, cyano, ester, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2. In some embodiments, the term "aryl group" is limited to substituted or unsubstituted aryl and heteroaryl rings having from three to 30 carbon atoms.

The term "aralkyl group" as used herein is an aryl group having an alkyl group or an alkylene group as defined herein covalently attached to the aryl group. An example of an aralkyl group is a benzyl group. "Optionally substituted aralkyl" refers to an optionally substituted aryl group covalently linked to an optionally substituted alkyl group or alkylene group. Such aralkyl groups are exemplified by benzyl, phenylethyl, 3-(4-methoxyphenyl)propyl, and the like.

The term "heteroaralkyl" refers to a heteroaryl group covalently linked to an alkylene group, where heteroaryl and alkylene are defined herein. "Optionally substituted heteroaralkyl" refers to an optionally substituted heteroaryl group covalently linked to an optionally substituted alkylene group. Such heteroalkyl groups are exemplified by 3-pyridylmethyl, quinolin-8-ylethyl, 4-methoxythiazol-2-ylpropyl, and the like.

The term "alkenyl group" refers to a monoradical of a branched or unbranched unsaturated hydrocarbon group typically having from 2 to 40 carbon atoms, more typically 2 to 10 carbon atoms and even more typically 2 to 6 carbon atoms and having 1-6, typically 1, double bond (vinyl). Typical alkenyl groups include ethenyl or vinyl (—CH=CH$_2$), 1-propylene or allyl (—CH$_2$CH=CH$_2$), isopropylene (—C(CH$_3$)=CH$_2$), bicyclo[2.2.1]heptene, and the like. When alkenyl is attached to nitrogen, the double bond cannot be alpha to the nitrogen.

The term "substituted alkenyl group" refers to an alkenyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "cycloalkenyl group" refers to carbocyclic groups of from 3 to 20 carbon atoms having a single cyclic ring or multiple condensed rings with at least one double bond in the ring structure.

The term "alkynyl group" refers to a monoradical of an unsaturated hydrocarbon, typically having from 2 to 40 carbon atoms, more typically 2 to 10 carbon atoms and even more typically 2 to 6 carbon atoms and having at least 1 and typically from 1-6 sites of acetylene (triple bond) unsaturation. Typical alkynyl groups include ethynyl, (—C≡CH), propargyl (or prop-1-yn-3-yl, —CH$_2$C≡CH), and the like. When alkynyl is attached to nitrogen, the triple bond cannot be alpha to the nitrogen.

The term "substituted alkynyl group" refers to an alkynyl group as defined above having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —SO$_2$-alkyl, SO$_2$-aryl and —SO$_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "alkylene group" is defined as a diradical of a branched or unbranched saturated hydrocarbon chain, having 1, 2, 3, 4, 5, 6, 7, 8, 9, 10, 11, 12, 13, 14, 15, 16, 17, 18, 19 or 20 carbon atoms, typically 1-10 carbon atoms, more typically 1, 2, 3, 4, 5 or 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

The term "substituted alkylene group" refers to: (1) an alkylene group as defined above having 1, 2, 3, 4, or 5 substituents selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, —$SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2; or (2) an alkylene group as defined above that is interrupted by 1-20 atoms independently chosen from oxygen, sulfur and $NR_a$—, where $R_a$ is chosen from hydrogen, optionally substituted alkyl, cycloalkyl, cycloalkenyl, aryl, heteroaryl and heterocyclyl, or groups selected from carbonyl, carboxyester, carboxyamide and sulfonyl; or (3) an alkylene group as defined above that has both 1, 2, 3, 4 or 5 substituents as defined above and is also interrupted by 1-20 atoms as defined above. Examples of substituted alkylenes are chloromethylene (—CH(Cl)—), aminoethylene (—$CH(NH_2)CH_2$—), methylaminoethylene (—CH(NHMe)$CH_2$—), 2-carboxypropylene isomers (—$CH_2$CH($CO_2$H)$CH_2$—), ethoxyethyl (—$CH_2CH_2$O—$CH_2CH_2$—), ethylmethylaminoethyl (—$CH_2CH_2$N($CH_3$)$CH_2CH_2$—), and the like.

The term "alkoxy group" refers to the group R—O—, where R is an optionally substituted alkyl or optionally substituted cycloalkyl, or R is a group —Y—Z, in which Y is optionally substituted alkylene and Z is optionally substituted alkenyl, optionally substituted alkynyl; or optionally substituted cycloalkenyl, where alkyl, alkenyl, alkynyl, cycloalkyl and cycloalkenyl are as defined herein. Typical alkoxy groups are optionally substituted alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, trifluoromethoxy, and the like.

The term "alkylthio group" refers to the group $R_S$—S—, where $R_S$ is as defined for alkoxy.

The term "aminocarbonyl" refers to the group —C(O)$NR_NR_N$ where each $R_N$ is independently hydrogen, alkyl, aryl, heteroaryl, heterocyclyl or where both $R_N$ groups are joined to form a heterocyclic group (e.g., morpholino). Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "acylamino" refers to the group —$NR_{NCO}$C(O)R where each $R_{NCO}$ is independently hydrogen, alkyl, aryl, heteroaryl, or heterocyclyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "acyloxy" refers to the groups —O(O)C-alkyl, —O(O)C-cycloalkyl, —O(O)C-aryl, —O(O)C-heteroaryl, and —O(O)C-heterocyclyl. Unless otherwise constrained by the definition, all substituents may be optionally further substituted by alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "aryloxy group" refers to the group aryl-O— wherein the aryl group is as defined above, and includes optionally substituted aryl groups as also defined above.

The term "heteroaryloxy" refers to the group heteroaryl-O—.

The term "amino" refers to the group —$NH_2$.

The term "substituted amino" refers to the group —$NR_wR_w$ where each $R_w$ is independently selected from the group consisting of hydrogen, alkyl, cycloalkyl, carboxyalkyl (for example, benzyloxycarbonyl), aryl, heteroaryl and heterocyclyl provided that both $R_w$ groups are not hydrogen, or a group —Y—Z, in which Y is optionally substituted alkylene and Z is alkenyl, cycloalkenyl, or alkynyl. Unless otherwise constrained by the definition, all substituents may optionally be further substituted by 1-3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "carboxy" refers to a group —C(O)OH. The term "carboxyalkyl group" refers to the groups —C(O)O-alkyl or —C(O)O-cycloalkyl, where alkyl and cycloalkyl, are as defined herein, and may be optionally further substituted by alkyl, alkenyl, alkynyl, alkoxy, halogen, $CF_3$, amino, substituted amino, cyano, and —$S(O)_nR_{SO}$, in which $R_{SO}$ is alkyl, aryl, or heteroaryl and n is 0, 1 or 2.

The terms "substituted cycloalkyl group" or "substituted cycloalkenyl group" refer to cycloalkyl or cycloalkenyl groups having 1, 2, 3, 4 or 5 substituents, and typically 1, 2, or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-aryl, —SO-heteroaryl, —$SO_2$-alkyl, $SO_2$-aryl and —$SO_2$-heteroaryl. Unless otherwise constrained by the definition, all substituents may optionally be further substituted by 1, 2, or 3 substituents chosen from alkyl, carboxy, carboxyalkyl, aminocarbonyl, hydroxy, alkoxy, halogen, $CF_3$, amino, substituted amino, cyano, and —$S(O)_nR_{SO}$, where $R_{SO}$ is alkyl, aryl, or heteroaryl and n is 0, 1 or 2.

The term "conjugated group" is defined as a linear, branched or cyclic group, or combination thereof, in which p-orbitals of the atoms within the group are connected via delocalization of electrons and wherein the structure can be described as containing alternating single and double or triple bonds and may further contain lone pairs, radicals, or carbenium ions. Conjugated cyclic groups may comprise both aromatic and non-aromatic groups, and may comprise polycyclic or heterocyclic groups, such as diketopyrrolopyrrole. Ideally, conjugated groups are bound in such a way as to continue the conjugation between the thiophene moieties they connect. In some embodiments, "conjugated groups" is limited to conjugated groups having three to 30 carbon atoms.

The term "halogen," "halo," or "halide" may be referred to interchangeably and refer to fluoro, bromo, chloro, and iodo.

The term "heterocyclyl" refers to a monoradical saturated or partially unsaturated group having a single ring or multiple condensed rings, having from 1 to 40 carbon atoms and from 1 to 10 hetero atoms, typically 1, 2, 3 or 4 heteroatoms, selected from nitrogen, sulfur, phosphorus, and/or oxygen within the ring. Heterocyclic groups can have a single ring or multiple condensed rings, and include tetrahydrofuranyl, morpholino, piperidinyl, piperazino, dihydropyridino, and the like.

Unless otherwise constrained by the definition for the heterocyclyl substituent, such heterocyclyl groups can be optionally substituted with 1, 2, 3, 4 or 5, and typically 1, 2 or 3 substituents, selected from the group consisting of alkyl, alkenyl, alkynyl, alkoxy, cycloalkyl, cycloalkenyl, acyl, acylamino, acyloxy, amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO— alkyl, —SO-aryl, —SO-heteroaryl, —SO$_2$-alkyl, —SO$_2$-aryl and —SO$_2$-heteroaryl. Unless otherwise constrained by the definition, all substituents may optionally be further substituted by 1-3 substituents chosen from alkyl, carboxy, carboxyalkyl, aminocarbonyl, hydroxy, alkoxy, halogen, CF$_3$, amino, substituted amino, cyano, and —S(O)$_n$R$_{SO}$, where R$_{SO}$ is alkyl, aryl, or heteroaryl and n is 0, 1 or 2.

The term "thiol" refers to the group —SH. The term "substituted alkylthio" refers to the group —S— substituted alkyl. The term "arylthiol group" refers to the group aryl-S—, where aryl is as defined as above. The term "heteroarylthiol" refers to the group —S— heteroaryl wherein the heteroaryl group is as defined above including optionally substituted heteroaryl groups as also defined above.

The term "sulfoxide" refers to a group —S(O)R$_{SO}$, in which R$_{SO}$ is alkyl, aryl, or heteroaryl. The term "substituted sulfoxide" refers to a group —S(O)R$_{SO}$, in which R$_{SO}$ is substituted alkyl, substituted aryl, or substituted heteroaryl, as defined herein. The term "sulfone" refers to a group —S(O)$_2$R$_{SO}$, in which R$_{SO}$ is alkyl, aryl, or heteroaryl. The term "substituted sulfone" refers to a group —S(O)$_2$R$_{SO}$, in which R$_{SO}$ is substituted alkyl, substituted aryl, or substituted heteroaryl, as defined herein.

The term "keto" refers to a group —C(O)—. The term "thiocarbonyl" refers to a group —C(S)—.

As used herein, the term "room temperature" is 20° C. to 25° C.

Disclosed are compounds, compositions, and components that can be used for, can be used in conjunction with, can be used in preparation of, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A weight percent of a component, unless specifically stated to the contrary, is based on the total weight of the formulation or composition in which the component is included.

Organic semiconductors as functional materials may be used in a variety of applications including, for example, printed electronics, organic transistors, including organic thin-film transistors (OTFTs) and organic field-effect transistors (OFETs), organic light-emitting diodes (OLEDs), organic integrated circuits, organic solar cells, and disposable sensors. Organic transistors may be used in many applications, including smart cards, security tags, and the backplanes of flat panel displays. Organic semiconductors may substantially reduce cost compared to inorganic counterparts, such as silicon. Depositing OSCs from solution may enable fast, large-area fabrication routes such as various printing methods and roll-to-roll processes.

Organic thin-film transistors are particularly interesting because their fabrication processes are less complex as compared with conventional silicon-based technologies. For example, OTFTs generally rely on low temperature deposition and solution processing, which, when used with semiconducting conjugated polymers, can achieve valuable technological attributes, such as compatibility with simple-write printing techniques, general low-cost manufacturing approaches, and flexible plastic substrates. Other potential applications for OTFTs include flexible electronic papers, sensors, memory devices (e.g., radio frequency identification cards (RFIDs)), remote controllable smart tags for supply chain management, large-area flexible displays, and smart cards.

Solution-processed conjugated polymers have attracted intensive interest for electronic device manufacture (e.g., polymeric light-emitting diodes (PLEDs), polymer solar cells (PSCs), sensors, memory devices, etc.), and specifically, organic thin film transistors (OTFTs), due to their low cost, large area, and flexible material advantages.

Often, these electronic applications require patterning of the OSC conjugated polymer material and gate insulating material to prevent undesired high off-current and cross-talk among adjacent devices. Photolithography is the most common technique used for inorganic semiconductor devices. However, in the manufacture of OTFTs, contacting with aggressive solvents from photoresist development and plasma-atmospheres during etch processes may significantly damage organic semiconducting and gate insulating thin films, as well as the semiconductor-dielectric interfaces. Device performance would be negatively impacted after these patterning steps.

Previous attempts at developing UV-patternable OSC material have suffered from poor device-to-device reproducibility when scaled up to big-area device arrays, or difficulty in balancing the UV patterning efficiency of the OSC polymers and OTFT device performance.

Compared with previous crosslinking-based solutions, the present application describes a process by which (A) a donor group is reacted with a protected acceptor group to form a protecting group-containing OSC polymer; (B) the protecting group is removed from the OSC polymer by thermal annealing or UV irradiation to form H-bonding sites; and (C) fusing H-bonding sites of a first OSC polymer backbone with H-bonding sites of a second OSC polymer backbone to form π-π interactions between conjugated OSC polymers.

By removing the protecting groups and enabling hydrogen bonding, the hydrogen-bond sites on π-conjugated polymer backbones lead to closely packed polymer chains, resulting in insoluble OSC polymers. The increased stability in solubility is enabled by OSC polymers containing latent hydrogen-bonding sites which can be used to immobilize and/or pattern conjugated polymers directly. Furthermore, exposed hydrogen bonding sites can be utilized in OTFT-based gas sensors to improve selectivity and sensitivity.

Moreover, film deposition of conjugated polymers typically requires spin-coating, ink-jet printing or blade coating, all of which require good solubility in a processing solvent. However, rigid backbones of conjugated polymers retards their solubility in organic solvents, thereby necessitating a solubilizing side group, such as aliphatic, ether, or ester constituents.

As presented herein, one route to attain solution-processed OSC polymer films is a precursor approach, where solubilizing (i.e., protecting) groups are first introduced as side chains onto OSC polymer backbones to ensure solubility and then eliminated after the OSC polymer has been deposited as a film. Protecting groups may be selected from at least one of: tert-butoxycarbonyl (t-Boc), nitrobenzyl ester (NBE), ortho-nitrobenzyl (ONB), esters, ethers, xanthane, tetrahydropyranyl (THP), silyls, ketones, ketals, halogens, benzoins, coumarins, benzoquinolone, benzocoumarin, 7-nitroindoline, p-hydroxyphenacyl, or combinations thereof. In addition, retro Diels-Alder reactions may also be used to achieve immobilization/patterning of OSC polymers.

Specifically for t-Boc protecting groups (used for amines in organic synthesis), removal of t-Boc (after disposing the polymer as a film) involves liberation of carboxylic acid and amide groups to form stabilizing hydrogen bonds that improve film morphology, order, and density. As hydrogen-bonding sites are fused with π-conjugated polymer backbone, the π-π interactions between conjugated OSC polymers are strongly enhanced when the hydrogen-bonds are formed, resulting in OSC polymers of much lower solubility. Release of the t-Boc group itself also reduces the OSC polymer's solubility significantly. Because the t-Boc protecting group may be removed from the OSC polymer by thermal annealing or UV irradiation, it can be transformed into —COOH by eliminating gaseous isobutylene after thermal annealing.

Once the t-Boc is eliminated and the π-π interactions between conjugated OSC polymers are formed, the resultant film demonstrates excellent resistance to organic solvents, aqueous acids, and thermal treatments. The immobilized/patterned polymers often show improved device characteristics in OTFTs. Resulting OTFT-based sensors built on such OSC polymers formed via attachment and subsequent removable of the protecting groups described herein, display remarkable sensitivity and selectivity toward ammonia and volatile amines. Detection of ammonia and amines is possible to a level of a 10 parts-per-billion (ppb) threshold with the immobilized OSC polymers. In addition to ammonia and amines, protecting groups (e.g., t-Boc, etc.) may also be used in fluoride anion extractor applications, patterned fluorescence microfiber imaging, chromogenic sensing, colorimetric anion sensing, and color imaging.

Moreover, t-Boc can also improve extreme operating or processing conditions. For example, to increase solubility of polyaniline (PANT) acceptor in organic solvents, PANI is electron-spun with corrosive solvents (e.g., strong acids, such as $H_2SO_4$). However, when attached with a t-Boc protecting group, t-Boc PANI may be soluble in common organic solvents. Hydrochloric acid (HCl) treatment of t-Boc PANI fibers helps to remove the acid labile t-Boc groups. As a result, HCl-doped PANI fibers are successfully used in detecting gaseous ammonia. PANI is a family of conducting polymers which are attractive materials for use in sensors, actuators, and electrodes due to the redox properties and high conductivity.

In some examples, acceptors upon which protecting groups may be grafted include: diketopyrrolopyrrole (DPP), indigo, isoindigo, or combinations thereof (Scheme 1). t-BOC protecting group is shown in Scheme 1, though this may be replaced with other similarly linked protecting groups (disclosed above). Scheme 2 shows some examples of acceptors which may be used, where 'LG' is the leaving group.

Scheme 1

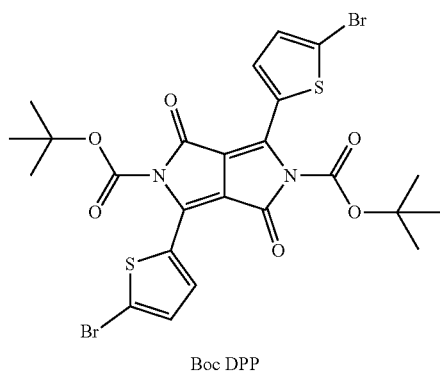

Boc DPP

13
-continued
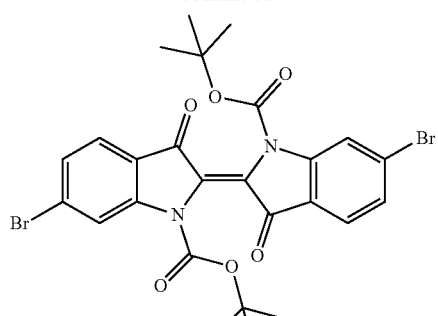
Boc Indigo
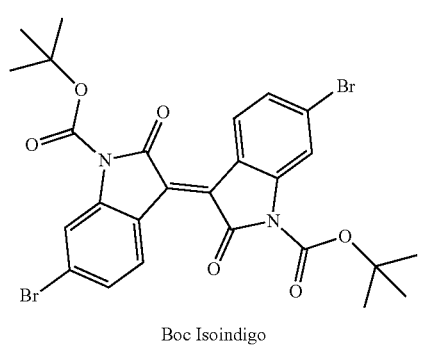
Boc Isoindigo
Scheme 2
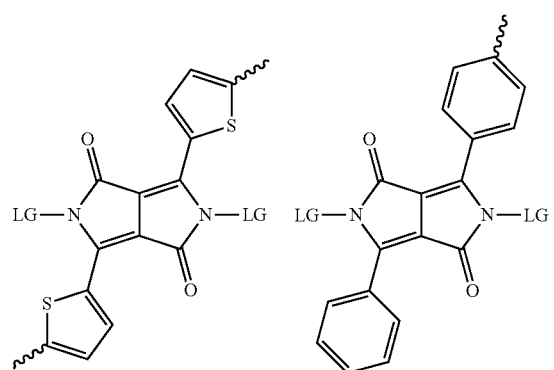
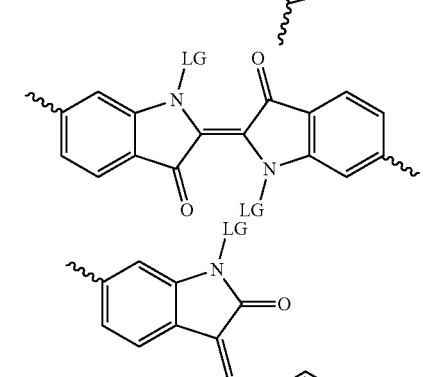
14
-continued
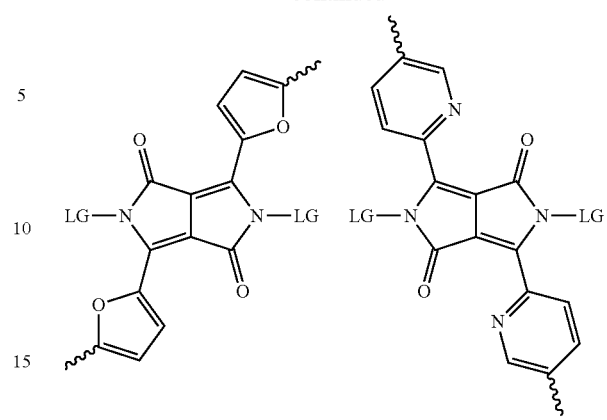
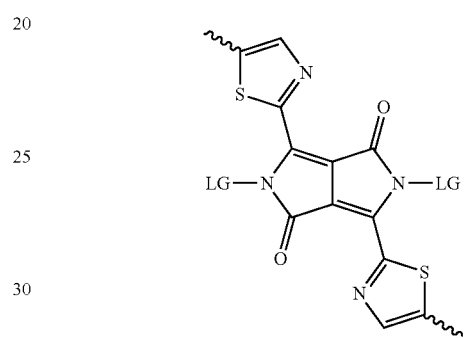
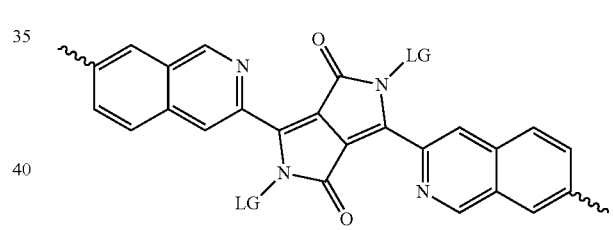
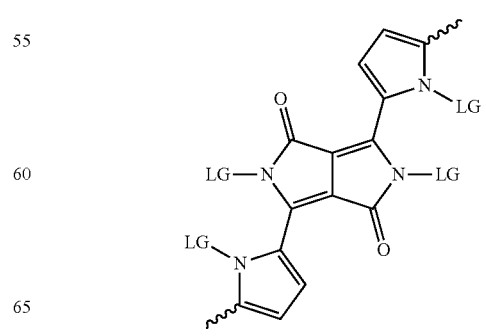

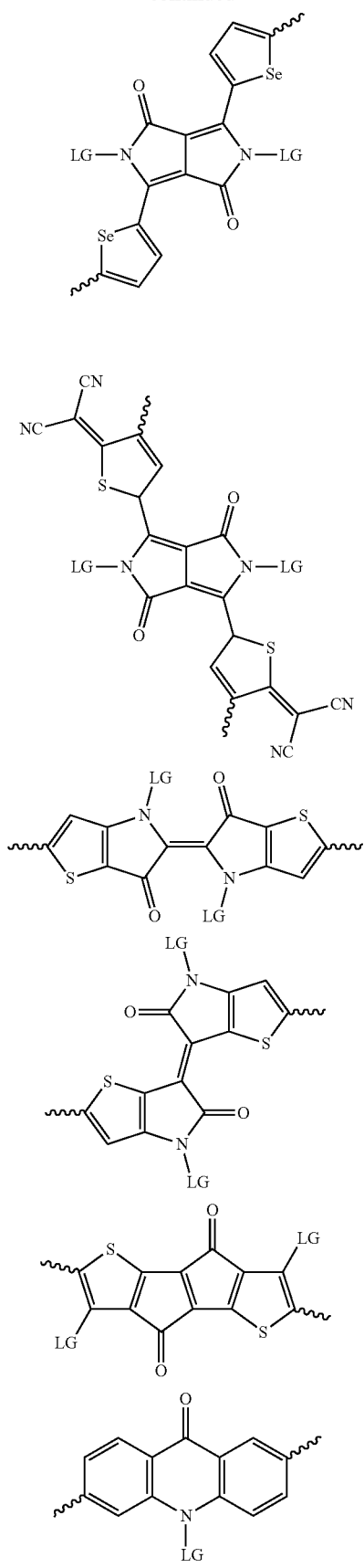
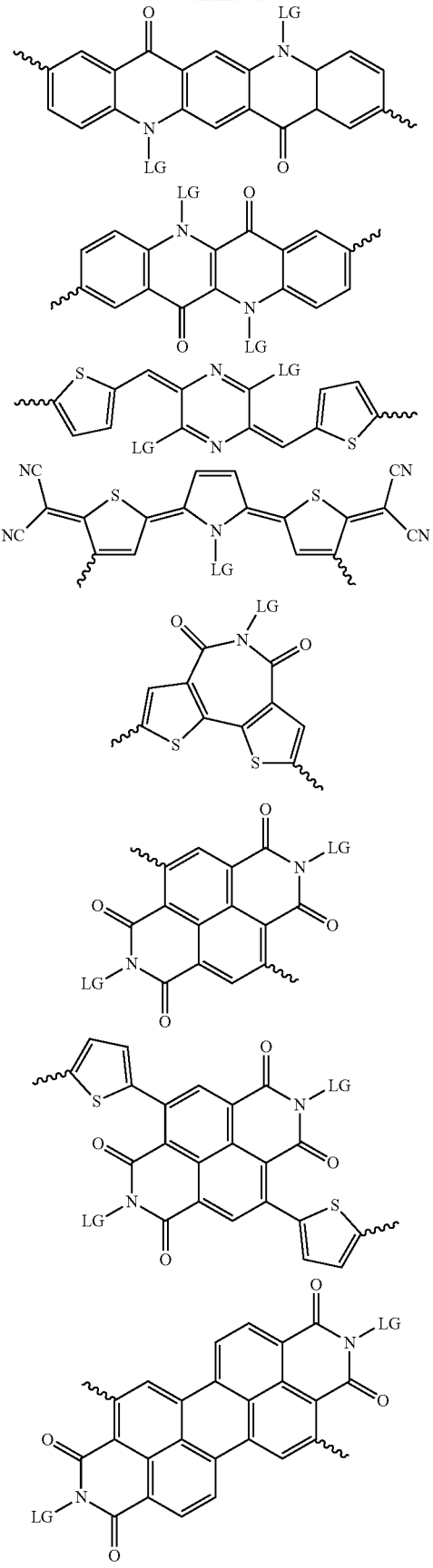

17
-continued
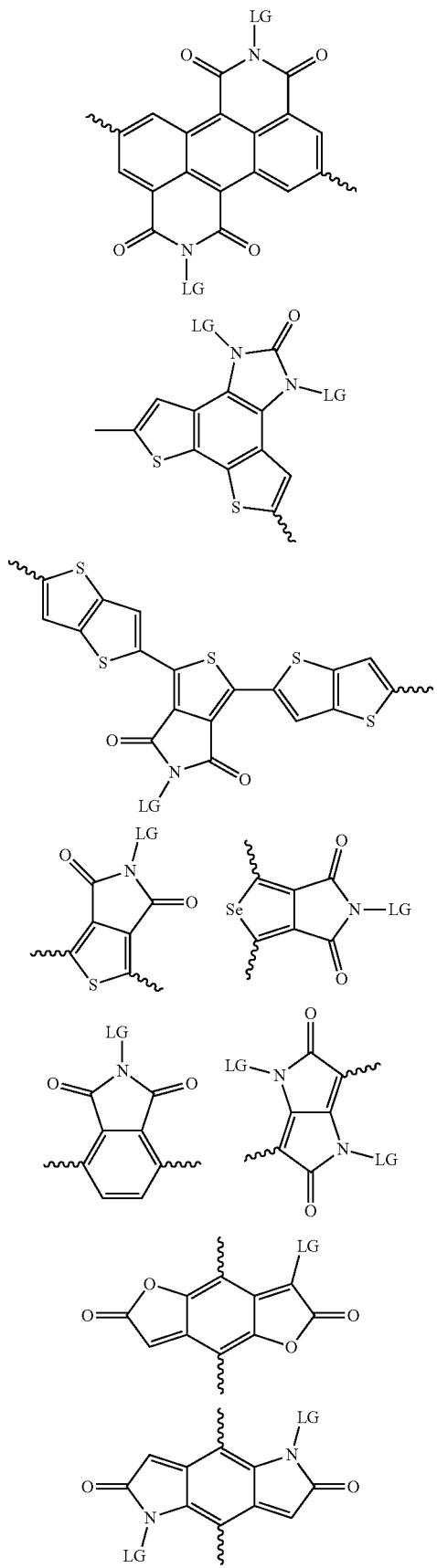
18
-continued
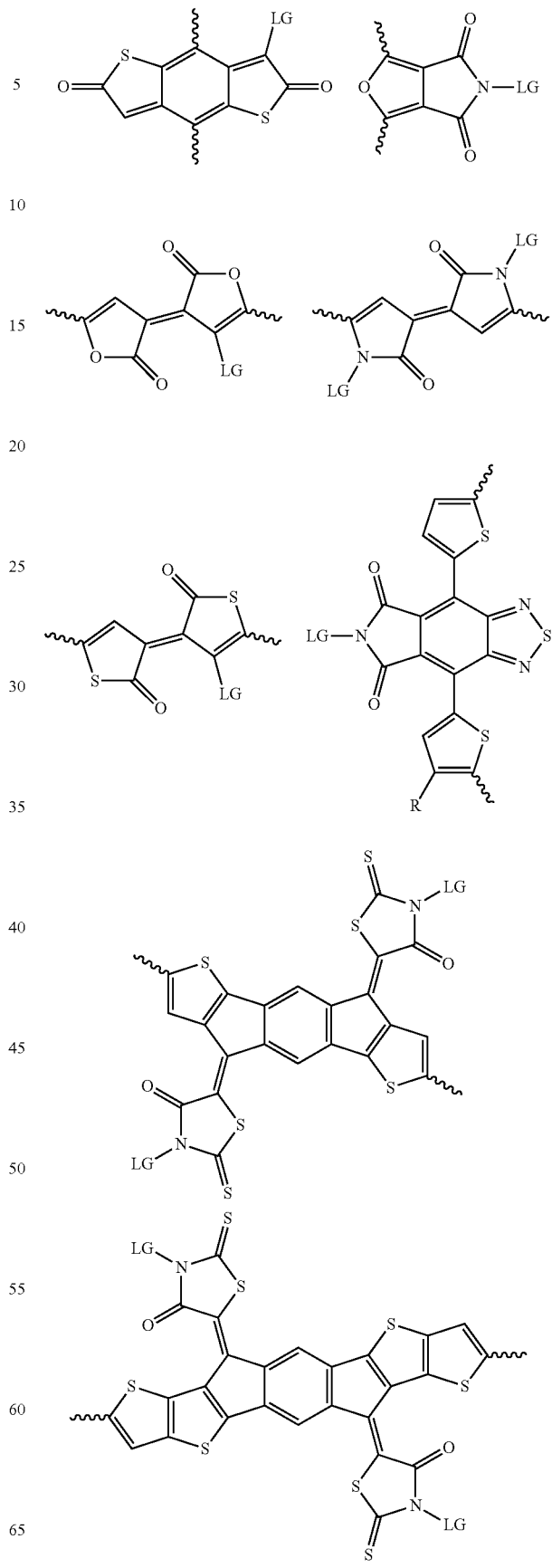

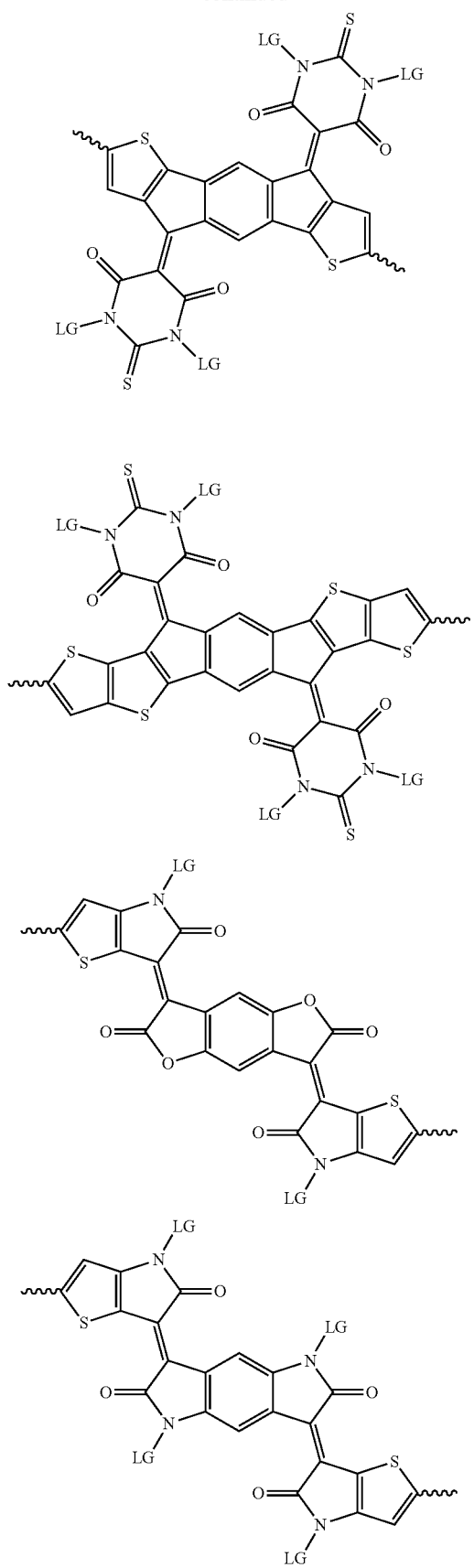
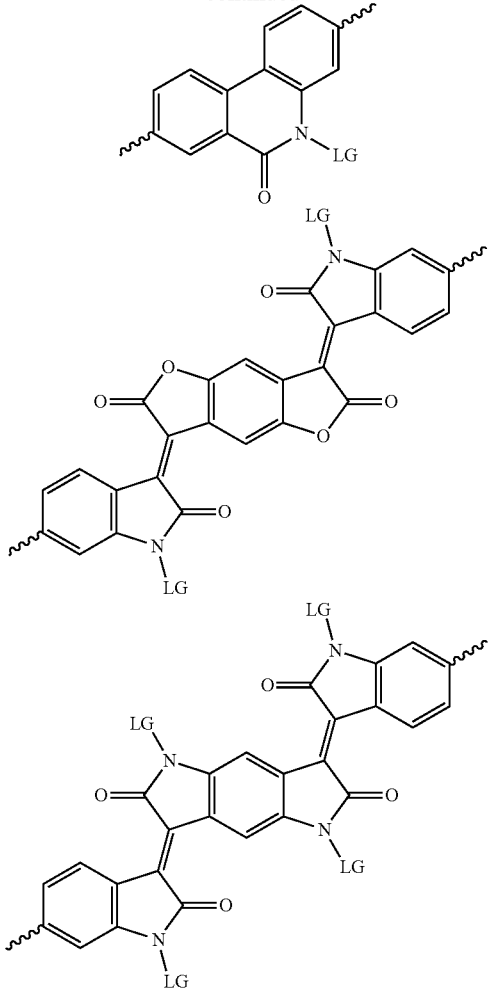
A series of donor-acceptor type of π-conjugated copolymers based on the acceptors described herein and the donors of Scheme 3 and 4 may be readily synthesized. In some examples, the donor is tetrathienoacene (FT4) (Scheme 3). Scheme 4 shows some examples of donors which may be used, where 'LG' is the leaving group.
Scheme 3
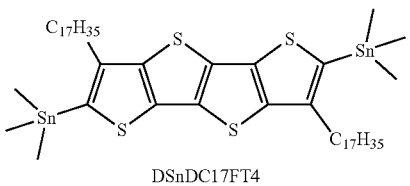
DSnDC17FT4
Scheme 4
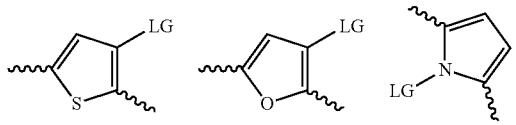

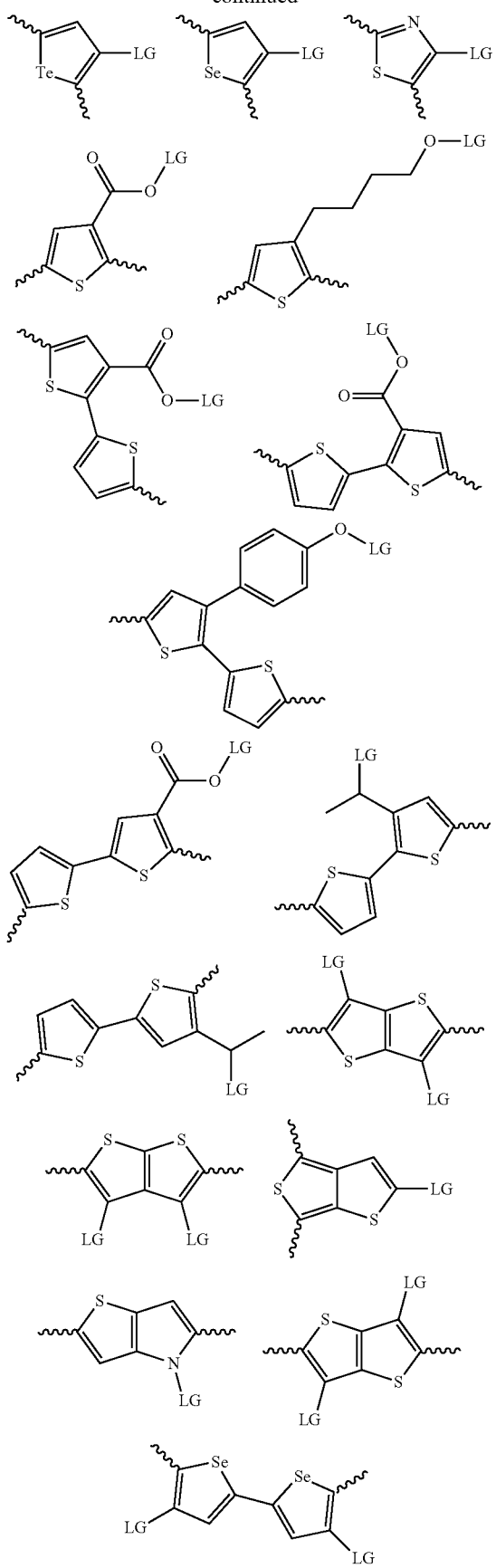
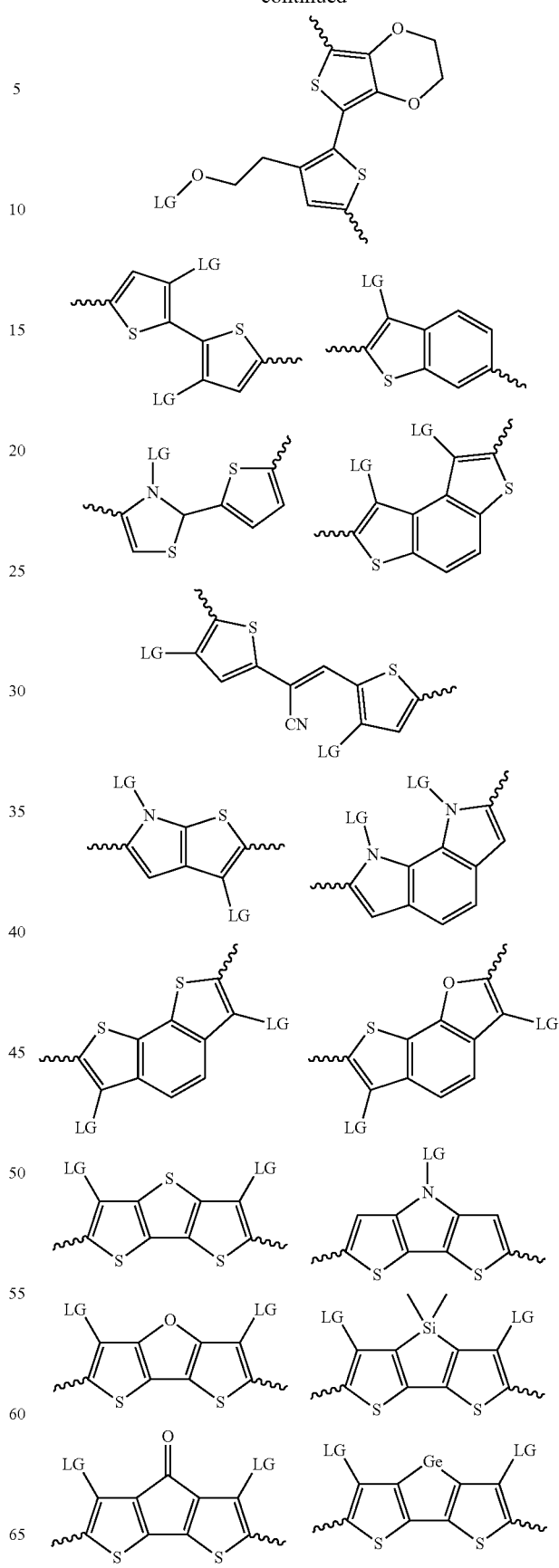

-continued
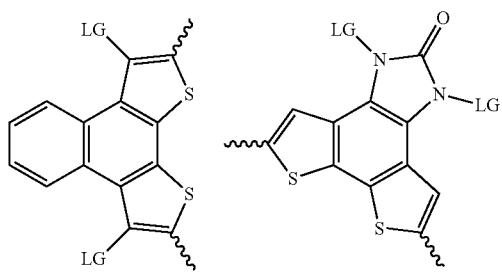
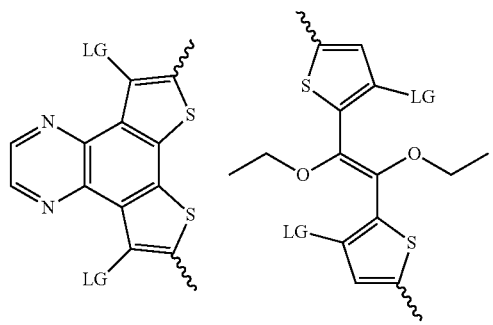
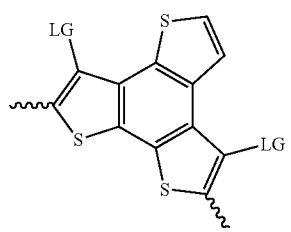
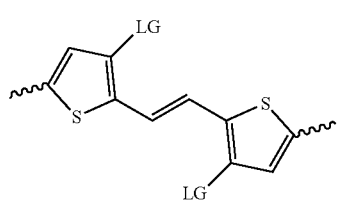
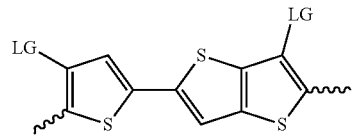
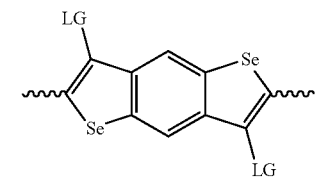
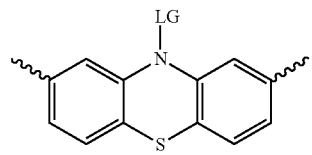
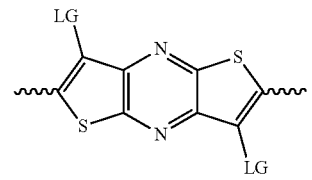
-continued
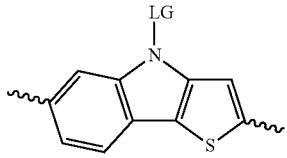
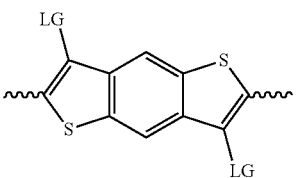
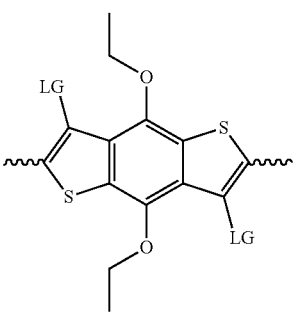
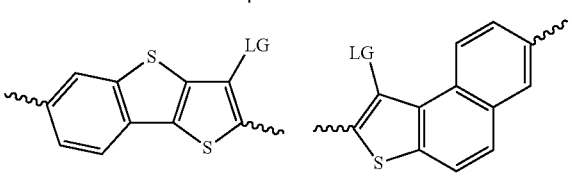
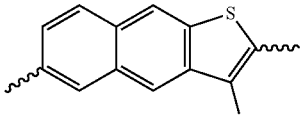
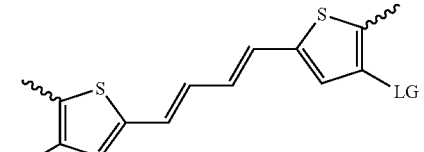
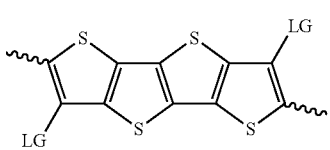
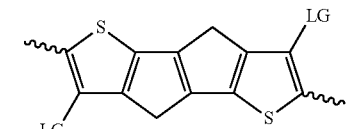
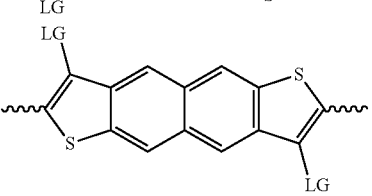

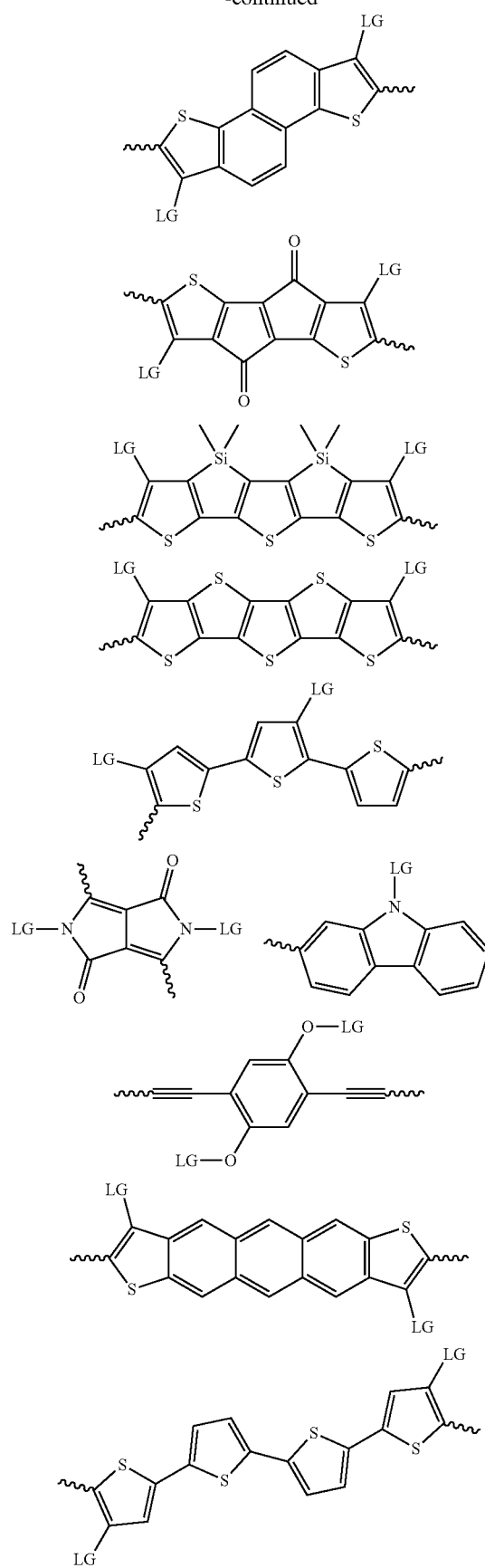
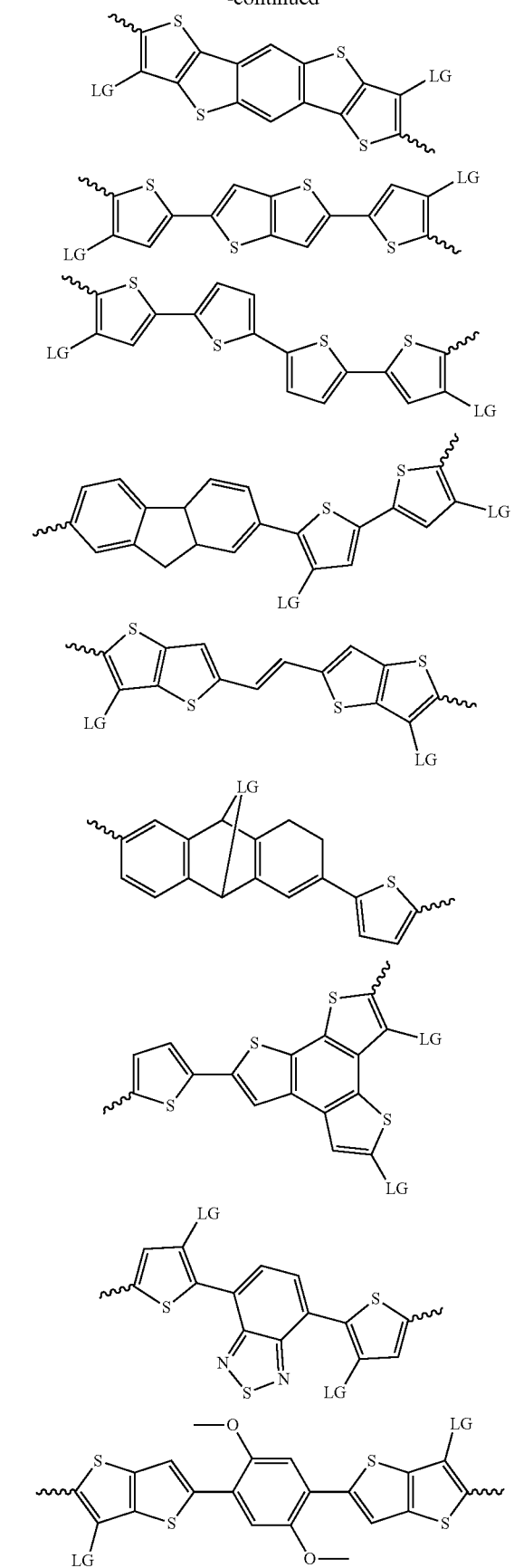

-continued

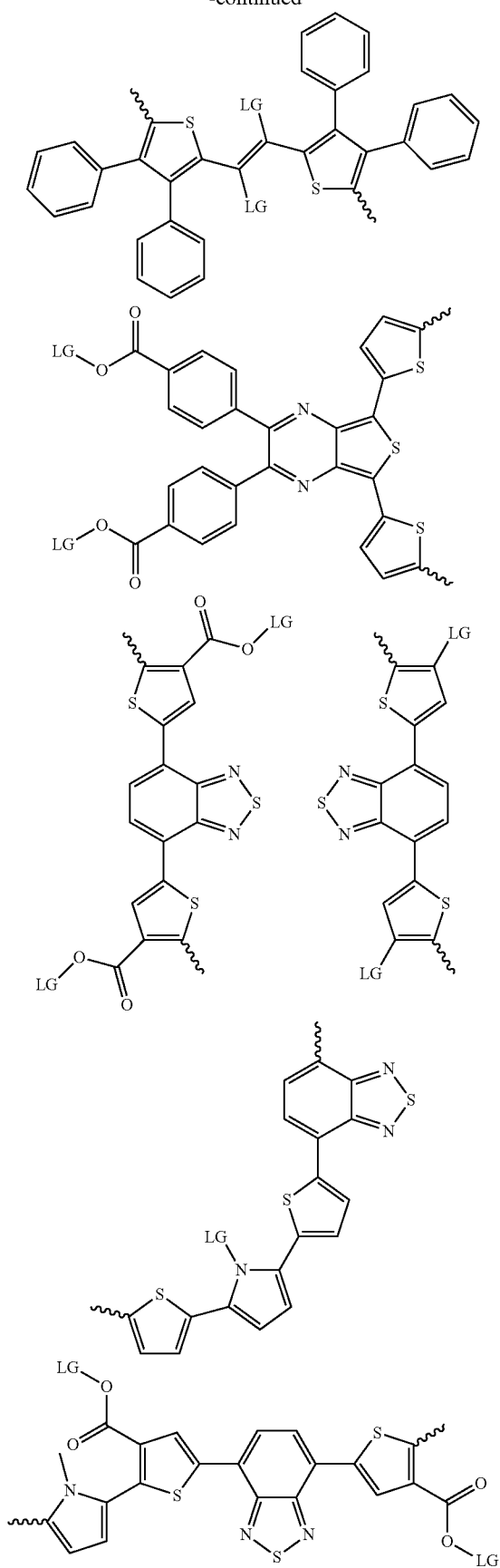

-continued

EXAMPLES

The embodiments described herein will be further clarified by the following examples.

All experimental operations are done in a fume hood unless otherwise stated.

Example 1—OSC Polymer Synthesis

Figure 5:
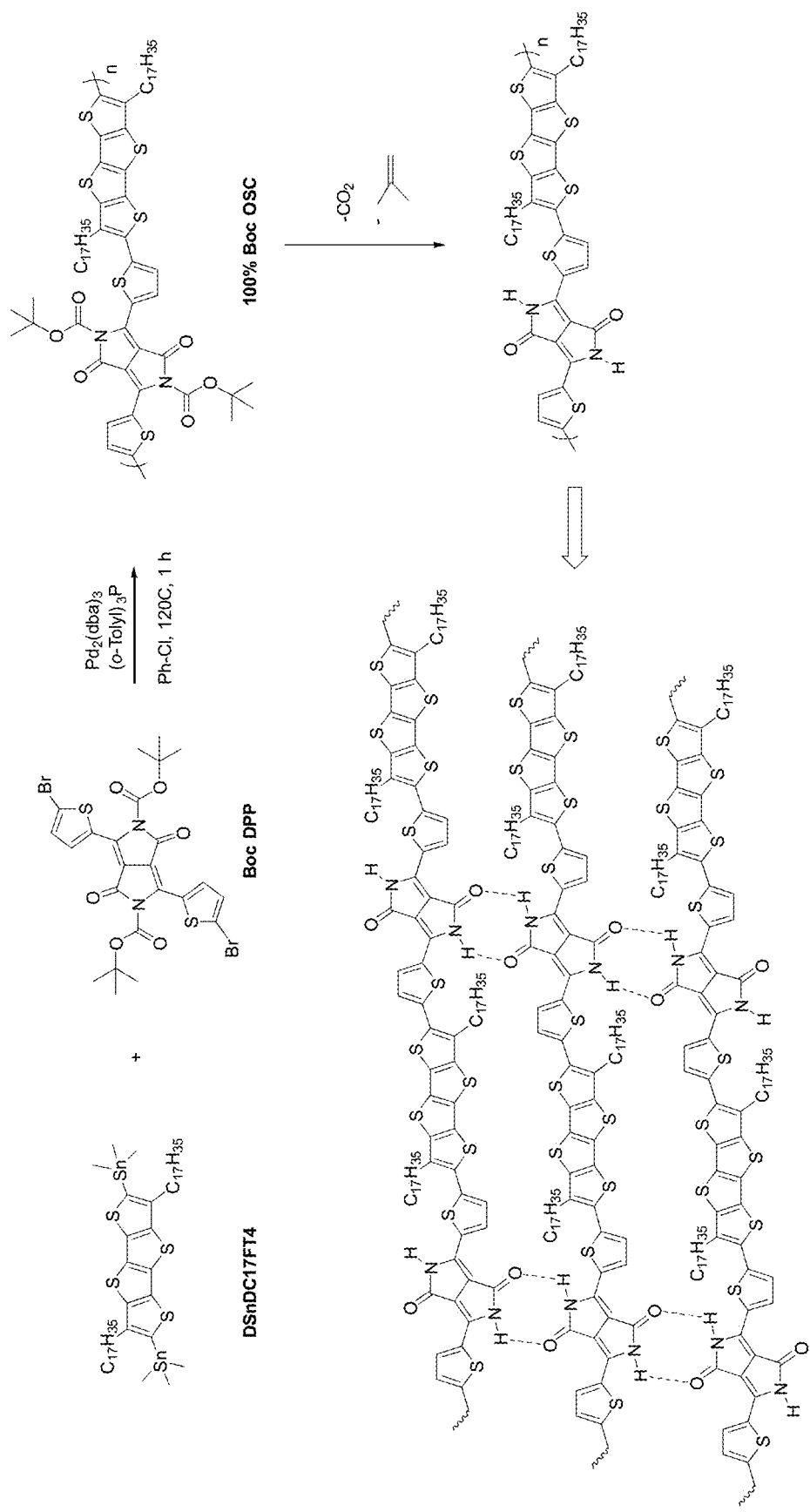
FIG. 5 is a scheme illustrating formation of OSC polymers by removal of protecting groups and hydrogen-bonding formation, according to some embodiments.

FIG. 5 is a scheme illustrating formation of OSC polymers by removal of protecting groups and hydrogen-bonding formation, according to some embodiments. The synthesis of Example 1 represents the first reaction step (synthesis procedure of 100% Boc OSC).

About a 1:1 mmol ratio of DSnDC17FT4-to-DPP monomer along with tris(dibenzylideneacetone)dipalladium(0) (Pd$_2$(DBA)$_3$) (catalyst) and tri(o-tolyl)phosphine (ligand of the catalyst) were weighed into the 3-neck round bottom flask. The round bottom flask is then vacuumed and filled with N$_2$ with Schlenk line manifold for three times. The reaction flask is then connected to a condenser and chlorobenzene (Ph-Cl, 20 mL) was added into the flask. A thermocouple was inserted into the reaction mixture through the septum in the third neck of the flask. The reaction mixture inner temperature was heated from room temperature to 120° C.

The reaction mixture is stirred in an oil bath for 1 hour after the inner temperature reaches 120° C. While the reaction mixture is still hot, it is directly poured into stirring 300 mL methanol. About 50 mL methanol is used to wash the flask. Conc. HCl (aq.) (4 mL) was added and the mixture is stirred overnight. The polymer is filtered from solution using a Buchner funnel and side arm conical flask with reduced pressure. Filtrate solution is discarded to hazardous waste.

The polymer is then transferred into a Soxhlet thimble and loaded into a Soxhlet extraction apparatus. Soxhlet extraction is run with acetone (300 mL) for 24 h. The acetone solution/suspension is discarded. Soxhlet extraction is run with n-hexane (300 mL) for 24 h. The hexane solution/suspension is discarded. The polymer is extracted into chloroform (300 mL) until no more material is dissolved. The polymer is precipitated by pouring the chloroform solution into a stirring beaker of acetone (400 mL), stirring at room temperature. The polymer is filtered from the solution using a Buchner funnel and side arm conical flask at reduced pressure. Filtrate solution is discarded. The polymer was dried under vacuum.

As shown in FIG. 5, 100% t-Boc DPP was initially used to synthesize the roughly 100% t-Boc OSC polymer (Polymer 1). Polymer 1 is not dissolved in 1,2,4-trichlorobenzene (e.g., 1 mg/mL at 120° C., see Table 1 below) and chlorobenzene.

One mechanism for removing the protecting group (second reaction step in FIG. 5) involves: (A) under acidic conditions, protons bind to the nitrogen atom on the amide bond, making it positively charged; (B) thereafter, the amide bond and the carbon-oxygen bond of the tert-butyl group are broken, generating tert-butyl carbocation and amine, and at the same time, releasing carbon dioxide; and (C) tert-butyl carbocation is deprotonated to form isobutene. With respect to the third reaction step of FIG. 5, where the H-bonding sites of a first OSC polymer backbone fuses with H-bonding sites of a second OSC polymer backbone to form $\pi$-$\pi$ interactions between conjugated OSC polymers, the hydrogen bond itself is a large delocalized $\pi$ bond. Hydrogen bonds improve $\pi$-$\pi$ stacking of OSC molecules and increase their crystallinity.

A similar mechanism as that provided herein and exemplified in FIG. 5 may also be used in the synthesis of cross-bred OSC polymers. For example, FIG. 6 utilizes an analogous reaction scheme, but using multiple variations of the DPP monomer, in this case, both t-Boc protected DPP monomer and a non-t-Boc protected DPP monomer (e.g., BC26DPP). Other and any number of variations may be used to achieve desired mechanical and chemical properties of the final OSC polymer. For example, multiple donors and multiple acceptors (e.g., protected acceptors, non-protected acceptors, and/or combinations thereof) may be used to tailor a final OSC polymer with desired solubility characteristics.

Example 2—Characterization

Molecular Weight Determination of Final OSC Polymer

Gel Permeation Chromatography (GPC) analysis was performed using a Polymer Labs (i.e., Agilent) GPC 220 system with a refractive index detector. The column used was a Resipore 300×7.5 mm. The mobile phase was 1,2,4-trichlorobenzene with a flow rate of 1 mL/min. All samples were prepared at 1 mg/mL in 1,2,4-trichlorobenzene. Loop volume was 100 μL. The system was calibrated with, and all results were comparative to, polystyrene standards with peak molecular weights of 10,110; 21,810; 28,770; 49,170; 74,800; 91,800; 139,400; and 230,900. Standard system temperature for measurement for molecular weights of fused thiophene based polymers was 200° C.

Figure 6:
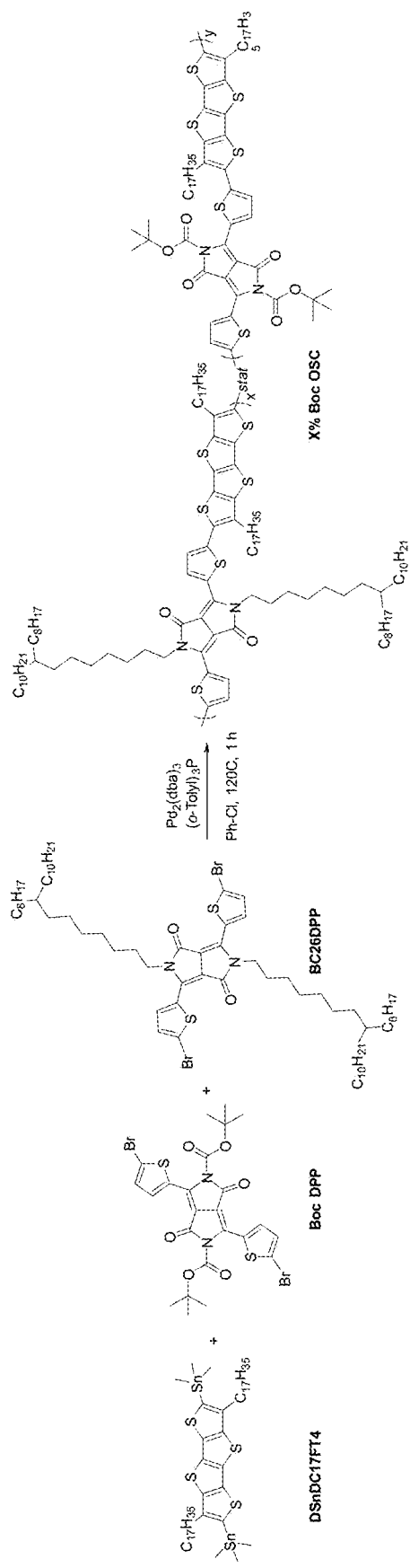
FIG. 6 is a scheme illustrating synthesis of cross-bred OSC polymers with reduced proportions of t-Boc DPP monomers, according to some embodiments.

Table 1 describes the molecular weights of t-Boc protected OSC polymers with the indicated proportion of reactants from the mechanisms of FIGS. 5 and 6. Mn is the number average molecular weight, which is a statistical average molecular weight of all polymer chains in the sample. Mw is the weight average molecular weight, which takes into account the molecular weight of a chain in determining contributions to the molecular weight average. In other words, the larger the polymer chain, the more that chain contributes to Mw. The ratio of Mw:Mn is the polydispersity index (PDI). So, for example, if all polymer chains are exactly the same, then the Mn and Mw would be exactly the same and the PDI is 1; the larger the PDI, the wider the molecular weight distribution. Table 1 indicates the trend that with decreasing t-BOC-to-DPP ratios, higher molecular weights are formed. In some examples, polymers with molecular weights greater than a predetermined threshold (e.g., 25,000) have shown good performance in for gas sensor applications.

TABLE 1

| Polymer | Final Yield (% t-Boc OSC Polymer) | Reactants | Mn | Mw | PDI |
| --- | --- | --- | --- | --- | --- |
| 1 | 100 | DSnDC17FT4 + 100% t-Boc DPP monomer (FIG. 5) | — | — | — |
| 2 | 50 | DSnDC17FT4 + 50% t-Boc DPP monomer + 50% BC26DPP monomer (FIG. 6) | 11374 | 21029 | 1.85 |
| 3 | 30 | DSnDC17FT4 + 30% t-Boc DPP monomer + 70% BC26DPP monomer (FIG. 6) | 22948 | 52130 | 2.27 |

Weight Loss Determination (Protecting Group Removal)

Figure 7A:
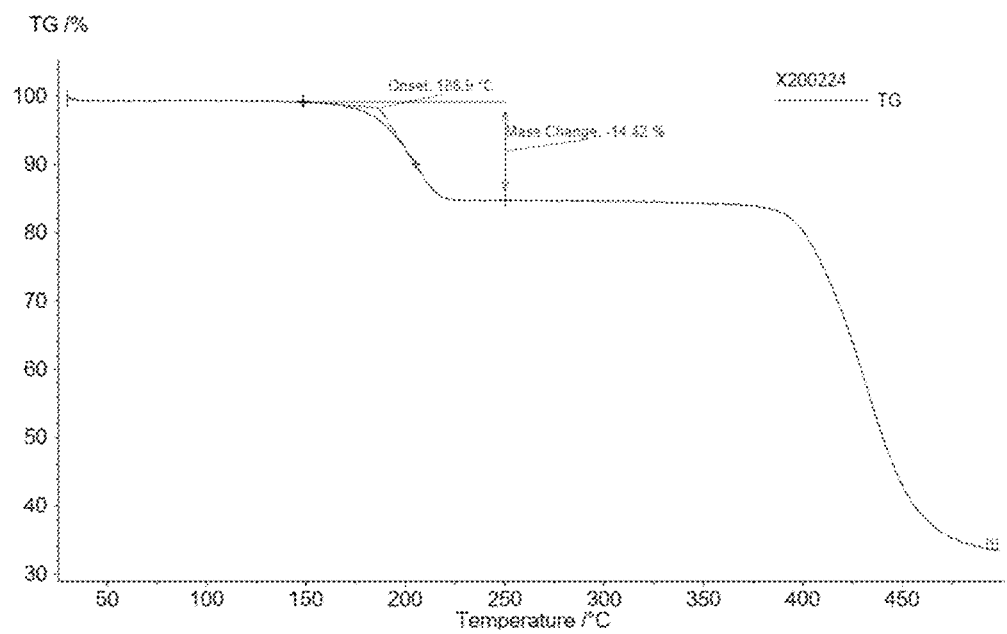
FIGS. 7A to 7C illustrate thermogravimetric analysis (TGA) of OSC polymers, according to some embodiments.
Figure 7B:
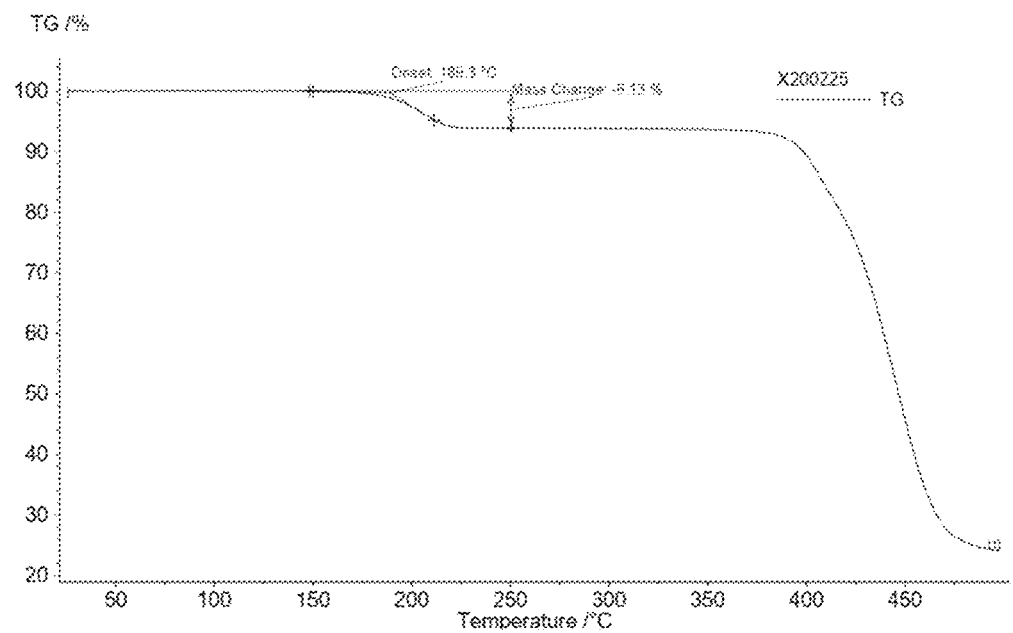
Figure 7C:
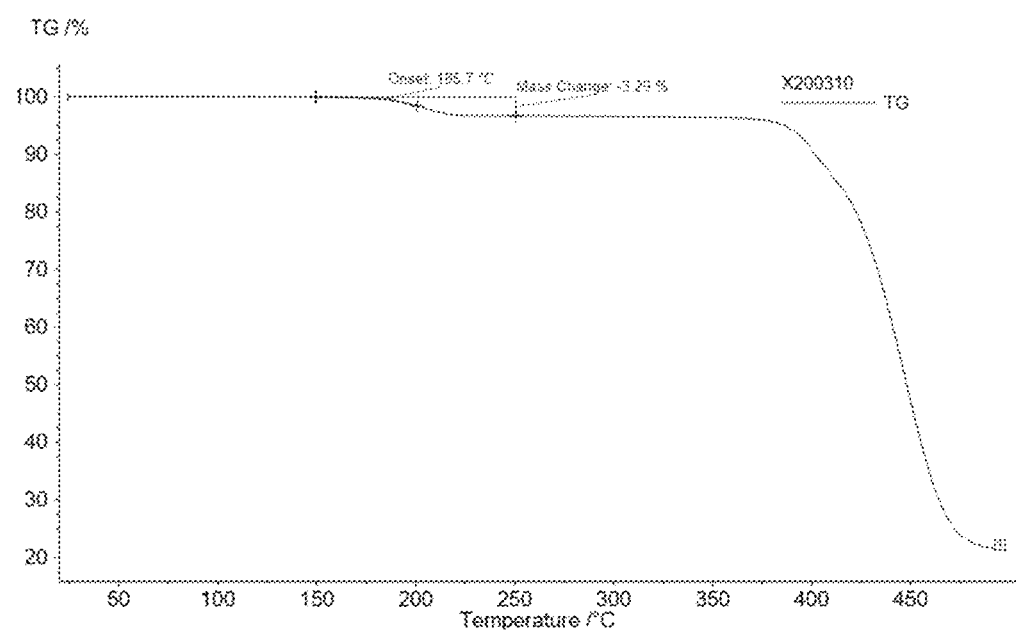

Thermogravimetric Analysis (TGA) was performed in a nitrogen flow (40 mL/min) in a temperature range of from 25° C. to 500° C., with a heating rate of 10° C./min. Thermal cleavage temperatures were determined to be between 186° C. to 189° C., as shown in FIGS. 7A to 7C for Polymers 1-3, respectively. The weight loss of Polymers 1-3 after thermal annealing (or UV irradiation) is 14.42%, 6.13%, and 3.29%, respectively. These values correspond well to the theoretical weigh percentage of t-Boc groups in Polymers 1-3 (e.g., 16.3%, 6.7%, and 3.7%, respectively). From this, it can be concluded that the weight loss of Polymers 1-3 is due to the removal of the t-Boc protecting group.

Lifetime Determination t-Boc OSC Polymers

Due to their inherent tendency to aggregate, the lifetime of OSC solutions is particularly important in ensuring uniformity and repeatability for industrial production. Here, solution lifetime of OSC polymers containing different proportions of t-Boc were investigated, with lifetime being defined as the duration of time till an OSC polymer solution begins to gel. Gelation is the phenomenon where the viscosity of a polymer solution gradually increases to become a gel state. The t-Boc OSC polymers were dissolved in chlorobenzene at 60° C. overnight. OSC polymers with 50% t-Boc at a concentration of 10 mg/mL in solution gelled almost immediately after cooling to room temperature (see Table 2). When concentration was reduced to 5 mg/mL, the solution retains its structural integrity for about one day and further, as concentration is continuously decreased to 3 mg/mL, although the solution does not gel even after two weeks, a significant increase in solution viscosity is observed. In comparison, the 30% t-Boc OSC polymer with a higher concentration (7 mg/mL) does not experience any gelation or viscosity increases within the same two week time period.

Polymers tested herein comprise long chain structures and random movement of chain segments cause entanglement—either with itself and/or other polymer chains—and leads to agglomeration. Especially for these types of conductive polymer, the agglomeration phenomenon is more obvious and due to this tendency, the polymer often forms a better crystallinity, which is conducive to carrier conduction. Comparing to the original alkyl side chain, the t-BOC group is too short to contribute to polymers' having high solubility. For example, 100% t-BOC OSC polymer contains 100% t-Boc side chains and is insoluble (see FIG. 5). Therefore, the t-Boc ratio must be decreased to increase solubility of OSC polymer. As shown in FIG. 6, cross-bred OSC polymers have a decreased t-BOC ratio and as a result, the long-branched side chains provide better solubility. The studies herein point to a balance between solubility of the precursor OSC and the drastic solubility change after removing protecting groups. In other words, if the solubility of the OSC polymer backbone is high, more t-BOC can be included without affecting solubility (i.e., t-BOC ratio can be high). In one example, for polymers having a FT4-DPP backbone, solubility is low and therefore, a certain concentration of long linear/branched alkyl side chains are needed to increase the solubility (e.g., a 30% to 50% ratio for the FT4-DPP OSC polymer).

TABLE 2

| Polymer | Concentration (mg/mL) | Lifetime (days) |
|---------|----------------------|-----------------|
| 2 | 10 | <1 |
| 2 | 5 | 1 |
| 2 | 3 | >14; significant increased viscosity |
| 3 | 7 | >14; no increase in viscosity |

Example 3—Immobilization and Patterning of OSC Polymers

Figures 8A, 8B, 8C:
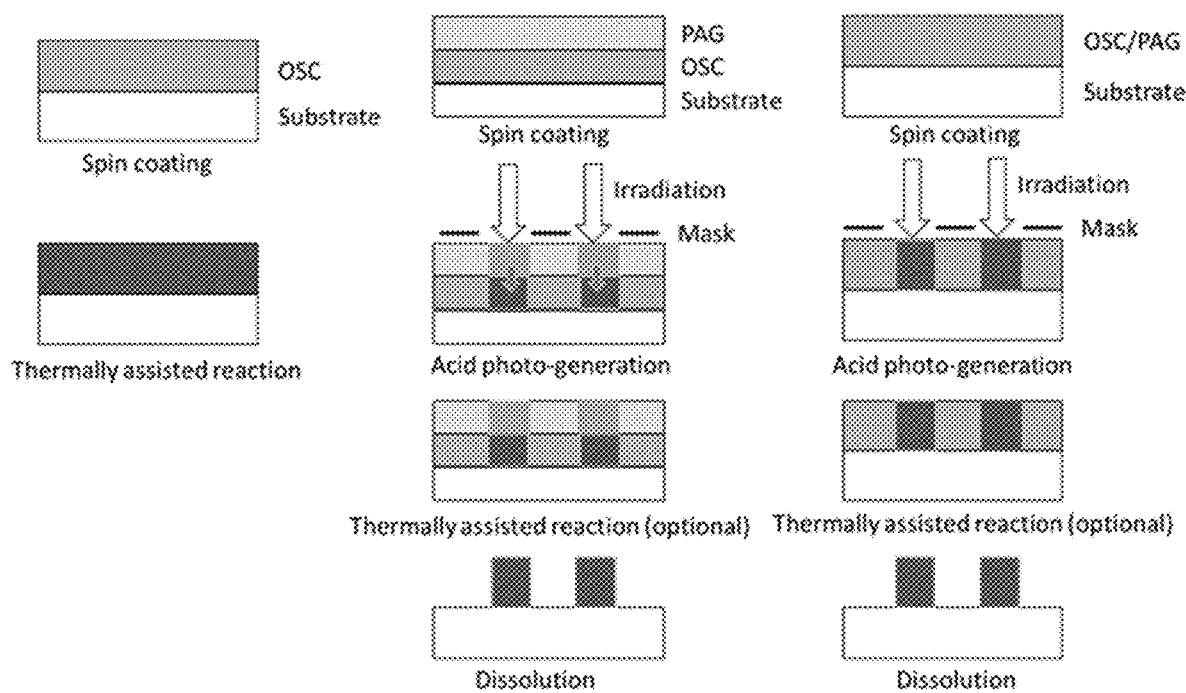
FIGS. 8A to 8C illustrate alternate pathways for solubility changes of t-Boc OSC polymers, according to some embodiments.

To understand solubility changes of t-Boc OSC polymers, three different immobilization and patterning schemes were tested, as shown in FIGS. 8A to 8C. As a control, in each of FIGS. 8A to 8C, Polymer 2 (formed by reaction between DSnDC17FT4+50% t-Boc DPP monomer+50% BC26DPP monomer) was used at a concentration of 3 mg/mL. All of Paths A, B, and C are conducted in air.
Path A: FIG. 8A
Polymer 2 was dissolved in chlorobenzene at a concentration of 3 mg/mL at 60° C. overnight. Thereafter, the OSC polymer solution was spin coated on glass after cooling to room temperature. After deposition, t-Boc protective groups from the t-Boc OSC polymers may be removed by thermal annealing at a temperature in a range of 100° C. to 500° C. (e.g., 130° C. to 230° C.), or 100° C. to 250° C., or 250° C. to 500° C. (or any sub-range or value therein) for a time in a range of 10 sec to 1 hr (e.g., 2 min to 30 min), or 2 min to 45 min, or 15 min to 45 min (or any sub-range or value therein). Dissolution tests were conducted using (I) a chlorobenzene wash; (II) pre-baking at 80° C.+a chlorobenzene wash; and (III) pre-baking at 80° C./2 min+annealing at 150° C./15 min+a chlorobenzene wash. The pre-baking is to evaporate the solvent to get a dried film. At conditions (I) and (II), the OSC polymer washed from the glass surface, indicating that baking at 80° C. does not remove the protecting group, as the solubility of the OSC polymer does not change. At condition (III), the OSC polymer was insoluble, indicating that the additional baking at 150° C. can remove the protecting group, as the solubility substantially decreases after baking. Path A demonstrates that precursor OSC polymer can be immobilized by thermal treatment and that the protecting groups can only be removed by the annealing step at high temperatures (e.g., 150° C.). For applications not requiring patterning, thermal treatment of the OSC polymer is a facile approach to achieving immobilization.
Path B: FIG. 8B
Polymer 2 was dissolved in chlorobenzene at a concentration of 3 mg/mL at 60° C. overnight. Thereafter, the OSC polymer solution was spin coated on glass after cooling to room temperature. In some examples, a solution of photo-acid generator (PAG) was spin coated on top of the OSC polymer film to form a stack. There is no reaction between the OSC polymer solution and PAG. During UV irradiation, the PAG releases acid, which reacts with the OSC polymer and accelerates removal of the protecting groups in OSC polymer at low temperatures. For example, heat generated by the UV irradiation is sufficient to remove the protecting groups with acid; additional thermal treatment may not be necessary. Examples of PAG are shown in Scheme 5 (CAS No.).

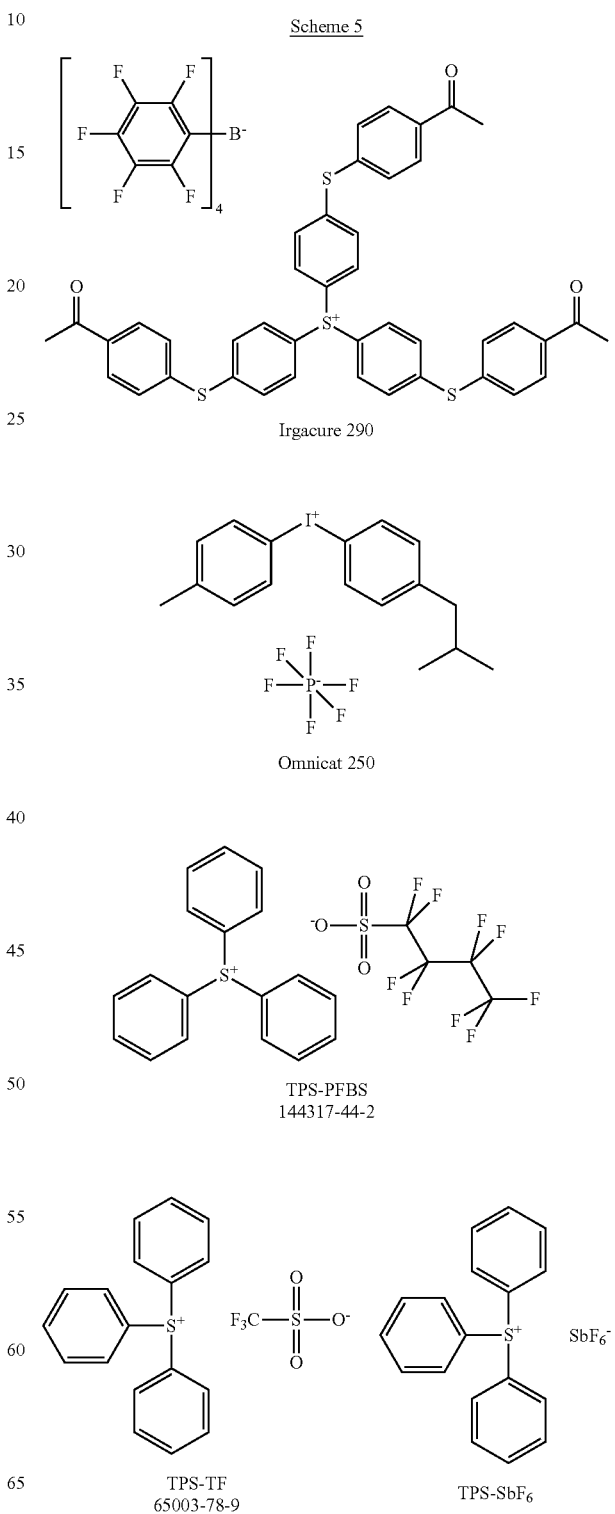

Scheme 5

-continued
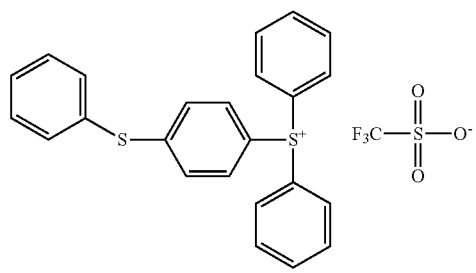
111281-12-0
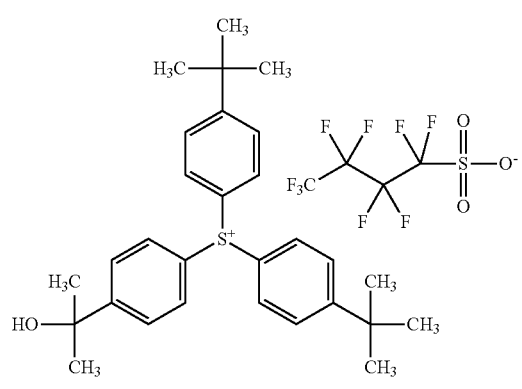
241806-75-7
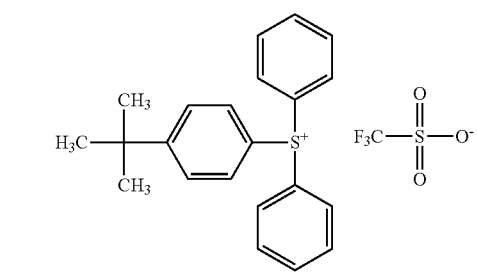
145612-66-4
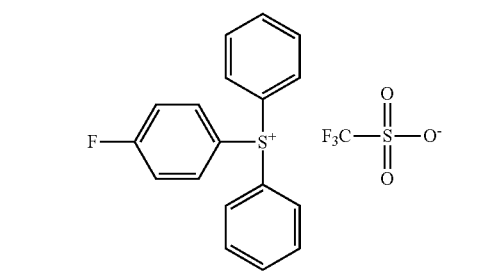
154093-57-9
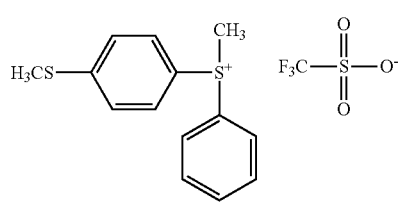
187868-29-7
-continued
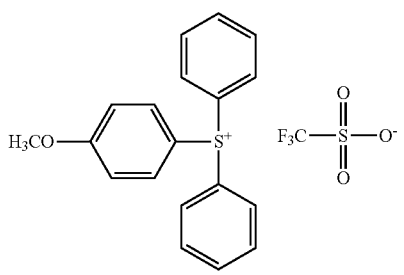
116808-67-4
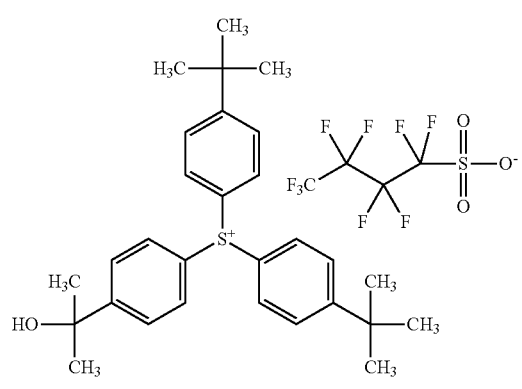
111281-12-0
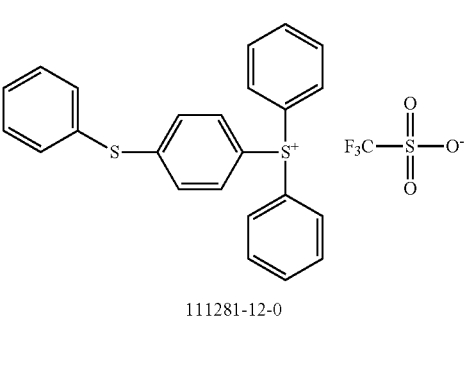
255056-46-3
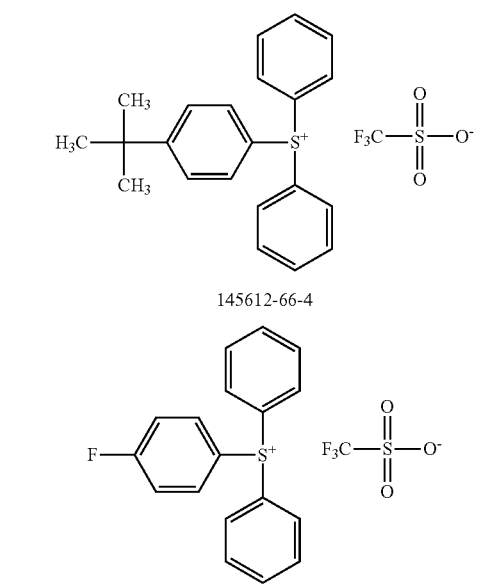
240482-96-6
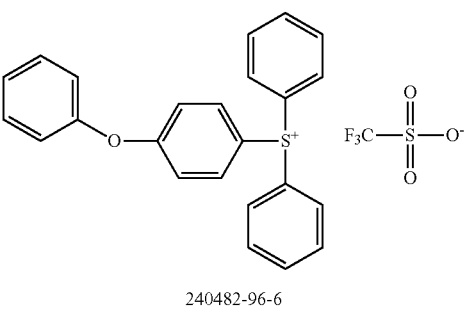
42573-57-9

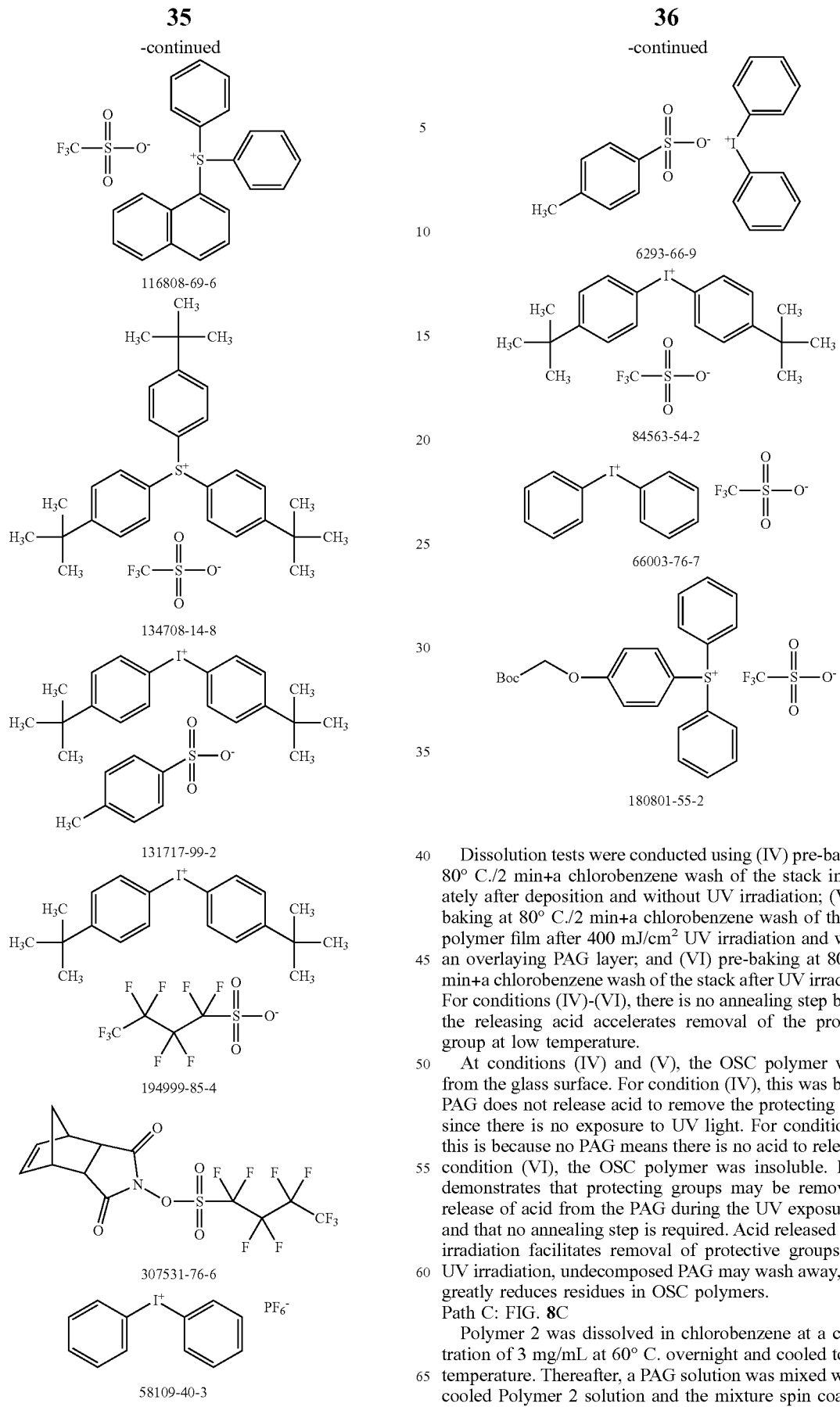

Dissolution tests were conducted using (IV) pre-baking at 80° C./2 min+a chlorobenzene wash of the stack immediately after deposition and without UV irradiation; (V) pre-baking at 80° C./2 min+a chlorobenzene wash of the OSC polymer film after 400 mJ/cm² UV irradiation and without an overlaying PAG layer; and (VI) pre-baking at 80° C./2 min+a chlorobenzene wash of the stack after UV irradiation. For conditions (IV)-(VI), there is no annealing step because the releasing acid accelerates removal of the protecting group at low temperature.

At conditions (IV) and (V), the OSC polymer washed from the glass surface. For condition (IV), this was because PAG does not release acid to remove the protecting groups since there is no exposure to UV light. For condition (V), this is because no PAG means there is no acid to release. At condition (VI), the OSC polymer was insoluble. Path B demonstrates that protecting groups may be removed by release of acid from the PAG during the UV exposure step and that no annealing step is required. Acid released by UV irradiation facilitates removal of protective groups. After UV irradiation, undecomposed PAG may wash away, which greatly reduces residues in OSC polymers.

Path C: FIG. 8C

Polymer 2 was dissolved in chlorobenzene at a concentration of 3 mg/mL at 60° C. overnight and cooled to room temperature. Thereafter, a PAG solution was mixed with the cooled Polymer 2 solution and the mixture spin coated on glass followed by exposure to 400 mJ/cm² UV irradiation.

Dissolution tests were conducted using (VII) pre-baking at 80° C./2 min+a chlorobenzene wash of the mixture after UV irradiation. There is no thermal annealing step at high temperatures, as the protecting group can be removed by the released acid generated from PAG with UV irradiation. At condition (VII), the OSC polymer was insoluble. Path C demonstrates that an alternative to condition (VI): the OSC polymer solution can also be mixed together with the PAG to achieve a similar result.

Each of Paths A, B, and C offer advantages for various situations. For example, if the application does not require patterning, Path A (condition (III)) is the best way to immobilize the OSC polymer. If the application does need patterning and cannot be heated at high annealing temperatures, either Path B (condition (VI)) or Path C (condition (VII)) is available. For condition (VII), the OSC polymer and PAG must be soluble in the same solvent. For condition (VI), different solvents may be used for casting the OSC polymer and PAG separately in two different solvents.

Example 4—UV Patterning of t-Boc OSC Polymers

In order to determine optimal UV irradiation conditions, for example, those incorporated in the immobilization and patterning procedures of Example 3, various UV light conditions were tested, as shown in Table 3 below.

Polymer 2 was dissolved in chlorobenzene at a concentration of 3 mg/mL at 60° C. overnight and cooled to room temperature. Thereafter, a PAG solution was mixed with the cooled Polymer 2 solution and the mixture spin coated on glass to form a film having a thickness in a range of 20-60 nm. After a pre-bake at 80° C. for 1 min, the film was exposed to 365 nm UV light having energies of 400 mJ/cm$^2$, 800 mJ/cm$^2$ and 1600 mJ/cm$^2$. After exposure, dissolution tests were conducted using a chlorobenzene wash for 4 min.

TABLE 3

| Sample | 1 | 2 | 3 | 4 |
|---|---|---|---|---|
| | Solution preparation: 3 mg/mL Polymer 2 in chlorobenzene solvent stirred at 60° C. overnight; cooled, then added to PAG solution | | | |
| | Spin coating: 500 rpm for 30 sec | | | |
| Pre-bake | 80° C. for 1 min | | | No pre-bake |
| UV light (365 nm) | 400 mJ/cm$^2$ | 800 mJ/cm$^2$ | 1600 mJ/cm$^2$ | 1600 mJ/cm$^2$ |
| Wash | Chlorobenzene for 4 min | | | |

FIGS. 9A to 9D illustrate ultraviolet (UV)-patterned images of t-Boc OSC polymers of Samples 1-4, respectively, in Example 4. As shown in FIGS. 9A to 9C for Samples 1-3, respectively, thought patterning improved (i.e., a greater amount of film exposed to UV light is shaped as desired) with an increase in energy, large-area residues are formed due to thermal pre-reaction between the OSC polymer and the PAG at the pre-baking step, thereby resulting in poor solubility of Polymer 2 in chlorobenzene. Based on this observation, Sample 4 was prepared without a pre-bake step and exposed to the higher energy UV light-1600 mJ/cm$^2$. Higher quality patterning images were obtained without problematic large-area residues.

Example 5—OTFT Device Fabrication

Conventional Technology: General Procedure

Applications using OTFT devices require patterning of organic semiconducting materials to prevent undesired high off-currents and crosstalk between adjacent devices. As explained above, photolithography is a common patterning technique in semiconductor device fabrication. However, photolithography usually involves harsh $O_2$ plasma during pattern transfer or photoresist removal and aggressive developing solvents which may severely damage the OSC layer and lead to significant deterioration of OTFT device performance. In other words, conjugated organic materials tend to degrade when exposed to light and the chemicals used in photolithography may have an adverse effect on organic thin film transistors. Therefore, patterning of organic semiconducting materials using photolithography is not practical.

FIGS. 1A to 1E illustrate traditional patterning techniques 100 of organic semiconductor blends utilizing photoresists. In a first step (FIG. 1A), a thin film 104 of the blended OSC polymer is deposited over a substrate 102 followed by deposition of a photoresist layer 106 thereon in FIG. 1B. Optionally, the thin film 104 may be thermally annealed. The photoresist deposition may be conducted using processes known in the art such as spin coating. For example, the photoresist, rendered into a liquid form by dissolving the solid components in a solvent, is poured onto the substrate, which is then spun on a turntable at a high speed producing the desired film. Thereafter, the resulting resist film may experience a post-apply bake process (i.e., soft-bake or prebake) to dry the photoresist in removing excess solvent.

In the step of FIG. 1C, the photoresist layer 106 is exposed to UV light 112 through a master pattern called a photomask 108 positioned some distance away from the photoresist layer 106 to form a higher crosslinked portion 110 of the photoresist layer 106. The exposure to UV light operates to change the solubility of the photoresist in a subsequent developer solvent solution for pattern formation atop the substrate. Prior to the developer, the resist layer may experience a post exposure bake. In the step of FIG. 1D, the pattern 116 of the photoresist layer is transferred into the thin film 104 via subtractive etching 114 (i.e., $O_2$ plasma dry etching). The patterned photoresist layer 116 "resists" the etching and protects the material covered by the photoresist. When the etching is complete, the photoresist is stripped (e.g., using organic or inorganic solutions, and dry (plasma) stripping) leaving the desired pattern 118 etched into the thin film layer.

However, as explained above, aspects of traditional photolithography processes such as harsh $O_2$ plasma during pattern transfer and aggressive photoresist developer solvents and/or stripping solvents may severely damage the OSC layer and lead to significant deterioration of device performance.

Current Technology: General Procedure

Figure 2B:
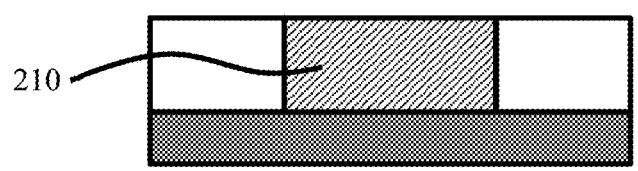
Figure 2C:
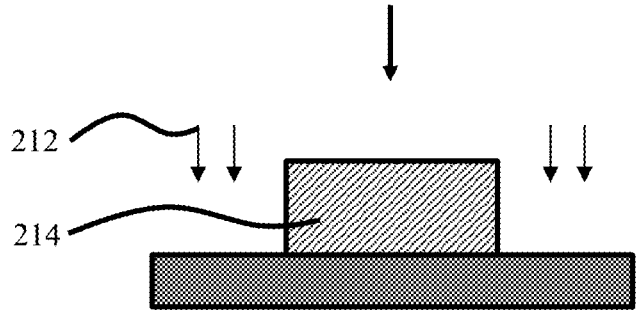

FIGS. 2A to 2C illustrate patterning techniques 200 of OSC polymers disclosed herein. In a first step (FIG. 2A), a thin film 204 of the OSC polymer is deposited over a substrate 202. Optionally, the thin film 204 may be thermally annealed. In some examples, depositing comprises at least one of spin coating; dip coating; spray coating; electrodeposition; meniscus coating; plasma deposition; and roller, curtain and extrusion coating. The thin film 204 comprises at least one organic semiconductor (OSC) polymer, and optionally, at least one PAG. The thin film may be prepared as explained in Example 1 (the OSC polymer) and Example 3 (immobilization and patterning).

In some examples, after the thin film of the OSC polymer is deposited over the substrate and before exposing the thin film to UV light, the thin film may be heated at a temperature in a range of 50° C. to 200° C. (e.g., 80° C.) for a time in a range of 10 sec to 10 min (e.g., 1 min) to remove excess solvent.

In a second step (FIG. 2B), the thin film 204 was exposed to UV light 208 through a photomask 206 to form a higher crosslinked portion 210 of the thin film 204. In some examples, the exposing comprises exposing the thin film to UV light having an energy in a range of 10 mJ/cm$^2$ to 2000 mJ/cm$^2$ (e.g., 400, 800, 1600, etc. mJ/cm$^2$), or 100 mJ/cm$^2$ to 1750 mJ/cm$^2$, 400 mJ/cm$^2$ to 1600 mJ/cm$^2$ for a time in a range of 1 sec to 60 sec, or 10 sec to 45 sec, or 1 sec to 30 sec, or 30 sec to 60 sec. Similar to photoresist functionality described in FIGS. 1A to 1E, the exposure to UV light operates to change the solubility of the thin film in a subsequent developer solvent solution for pattern formation atop the substrate.

In step FIG. 2C, when light exposure is complete, the portion of the thin film 204 not exposed to UV light 208 was stripped using a predetermined solvent 212, thereby leaving the desired pattern 214 into the thin film layer. In other words, the higher crosslinked portion 210 was developed in a solvent to remove an un-patterned region of the thin film 204. In some examples, the developing comprises exposing the un-patterned region of the thin film to a solvent comprising chlorobenzene, 1,2-dichlorobenzene, 1,3-dichlorobenzene, 1,2,4-trichlorobenzene, dioxane, p-xylene, m-xylene, toluene, cyclopentanone, cyclohexanone, methyl lactate, 2-butanone, 2-pentanone, 3-pentanone, 2-heptanone, 3-heptanone, anisole, mesitylene, decalin, butylbenzene, cyclooctane, tetralin, chloroform, or combinations thereof, for a time in a range of 10 sec to 10 min. In some examples, the developer solution comprises chlorobenzene, p-xylene, dioxane, or combinations thereof.

In some examples, after developing the patterned thin film in a solvent to remove the un-patterned region of the thin film, the thin film may be heated at a temperature in a range of 50° C. to 200° C. (e.g., 150° C.) for a time in a range of 10 sec to 30 min (e.g., 15 min).

Figure 3:
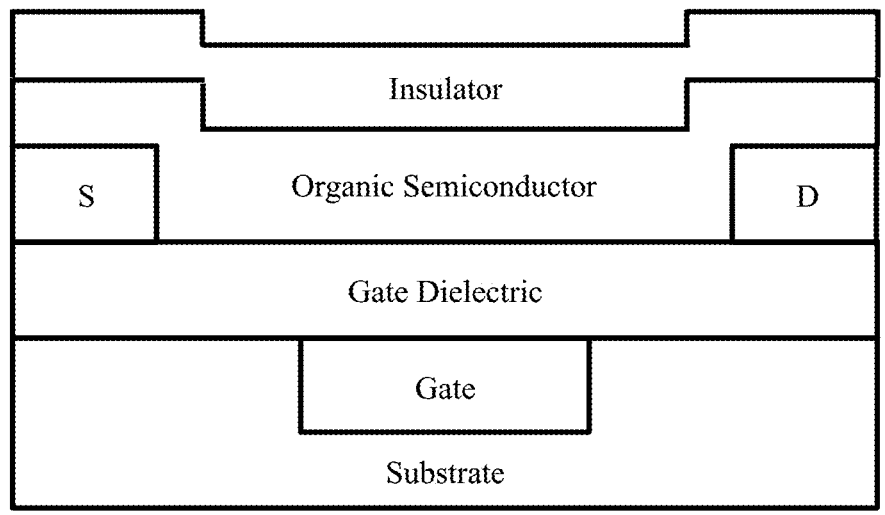
FIG. 3 illustrates an exemplary OTFT device, according to some embodiments.
Figure 4:
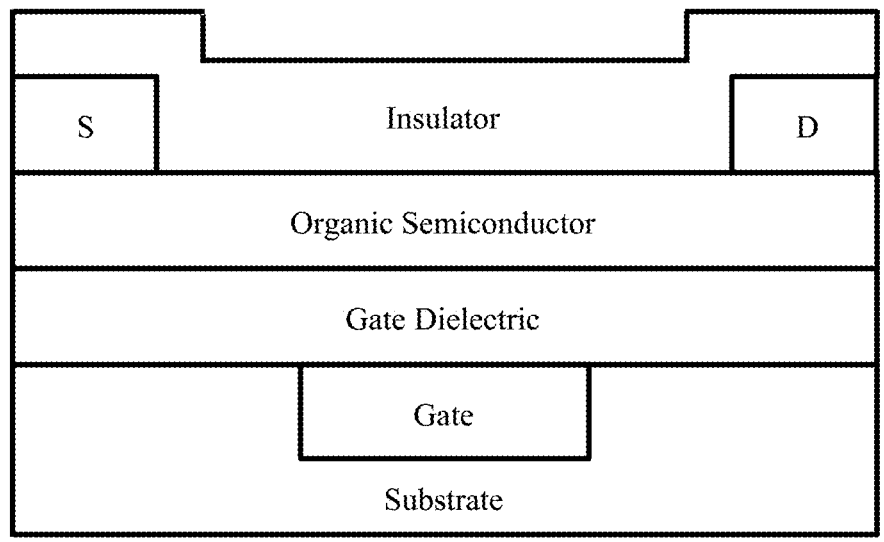
FIG. 4 illustrates an exemplary OTFT device, according to some embodiments.

Thereafter, the OTFT devices may be completed by forming a gate electrode over the substrate; forming a gate dielectric layer over the substrate; forming patterned source and drain electrodes over the gate dielectric layer; forming an organic semiconductor active layer over the and gate dielectric layer, and forming an insulator layer over the patterned organic semiconductor active layer. (FIGS. 3 and 4).

Example 6—General Manufacturing Procedure for OTFT Device

In some examples, a bottom gate, bottom contact OTFT device can be formed as following: patterning a gold (Au) or silver (Ag) gate electrode onto a substrate, followed by spin-coating a dielectric onto the substrate and treating to obtain a gate dielectric layer. After patterning Au or Ag source and drain electrodes, an OSC layer may be formed by the materials and methods of patterning as described herein to a thickness in a range of 10 nm to 200 nm. Finally, an insulator layer was positioned. One example of the formed OTFT device is shown in FIG. 3. Another example of a formed OTFT device is shown in FIG. 4, which the OSC layer formed directly atop the gate dielectric, followed by the source and drain electrodes provided thereon.

Thus, as presented herein, improved methods of formation for photo-patternable organic semiconductor polymers are disclosed for OSC layers of organo-electronic devices (e.g., OTFTs). In particular, a facile approach to immobilize and pattern OSC polymers is demonstrated. Conjugated OSC polymers with latent hydrogen-bonding sites on a main chain are synthesized and converted to OSC polymers containing actual hydrogen bonding sites. OSC polymers are processed based on a thermal annealing and/or UV irradiation process to remove protecting group on sidechains of the OSC polymers. By removing the protecting groups and forming hydrogen-bonding sites as a consequence, hydrogen-bond sites on π-conjugated polymer backbones lead to closely packed polymer chains, resulting in insoluble OSC polymers. This insoluble nature of the OSC polymers enables immobilization and patterning of the conjugated polymers directly in OTFT devices, such as OTFT-based gas sensors.

Advantages

The disclosed immobilization/patterning approach has at least the following advantages: (A) fused thiophene structures with t-Boc attached acceptors can form donor-acceptor OSC polymers; (B) t-Boc can be easily released through thermal annealing and/or UV irradiation processes; (C) compared with DPP monomers containing crosslinkable functional groups, which requires multiple steps of synthesis, DPP monomers containing removable t-Boc groups are efficiently synthesized with readily available raw materials, thereby reducing the OSC polymer's cost of manufacture significantly; (D) enhanced π-π stacking caused by hydrogen-bonding (from removal of protecting group) improves OTFT's performance; in comparison, crosslinkable OSC polymers experience distorted molecular chain packing, which causes deteriorated electronic device performance; (E) the OSC polymers contained herein (e.g., FIG. 5) comprise N—H functional groups after the thermal annealing and/or UV irradiation process removes the protecting group; besides patterning for display applications, the N—H bond provides additional sensitivity for chemical sensor applications; and (F) thermal annealing and/or UV irradiation t-Boc groups results in elimination of isobutylene and carbon dioxide and also formation of nanopores within the OSC thin film, the latter of which facilitates diffusion and interaction of chemical gases within the semiconducting layer, leading to high sensitivity and fast response of OTFT-based gas sensors.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. The indefinite article "a" or "an" and its corresponding definite article "the" as used herein means at least one, or one or more, unless specified otherwise.

References herein to the positions of elements (e.g., "top," "bottom," "above," "below," etc.) are merely used to describe the orientation of various elements in the FIG- URES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be apparent to those skilled in the art that various modifications and variations can be made without departing from the spirit or scope of the claimed subject matter. Accordingly, the claimed subject matter is not to be restricted except in light of the attached claims and their equivalents.

What is claimed is:

1. A method, comprising:
   reacting at least one donor group with at least one protected acceptor group to form a plurality of protecting group-containing OSC polymers;
   removing the protecting group from the plurality of protecting group-containing OSC polymers to form H-bonding sites; and
   fusing the H-bonding sites of a first OSC polymer backbone with H-bonding sites of a second OSC polymer backbone to form π-π interactions between conjugated OSC polymers,
   wherein the at least one donor group is:

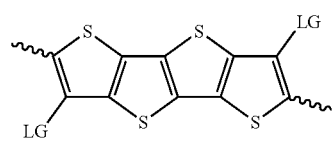

wherein LG represents a lipophilic group.

2. The method of claim 1, wherein the step of removing is conducted by thermal annealing, UV irradiation, or a combination thereof.

3. The method of claim 1, wherein the at least one donor group is tetrathienoacene (FT4)

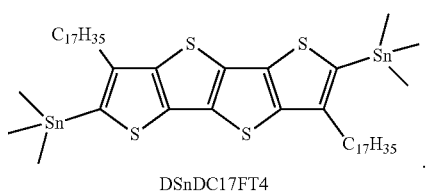

DSnDC17FT4

4. The method of claim 1, wherein the at least one protected acceptor group is selected from at least one of: diketopyrrolopyrrole (DPP), indigo, isoindigo, or combinations thereof.

5. The method of claim 1, wherein the at least one protected acceptor group is selected from at least one of:

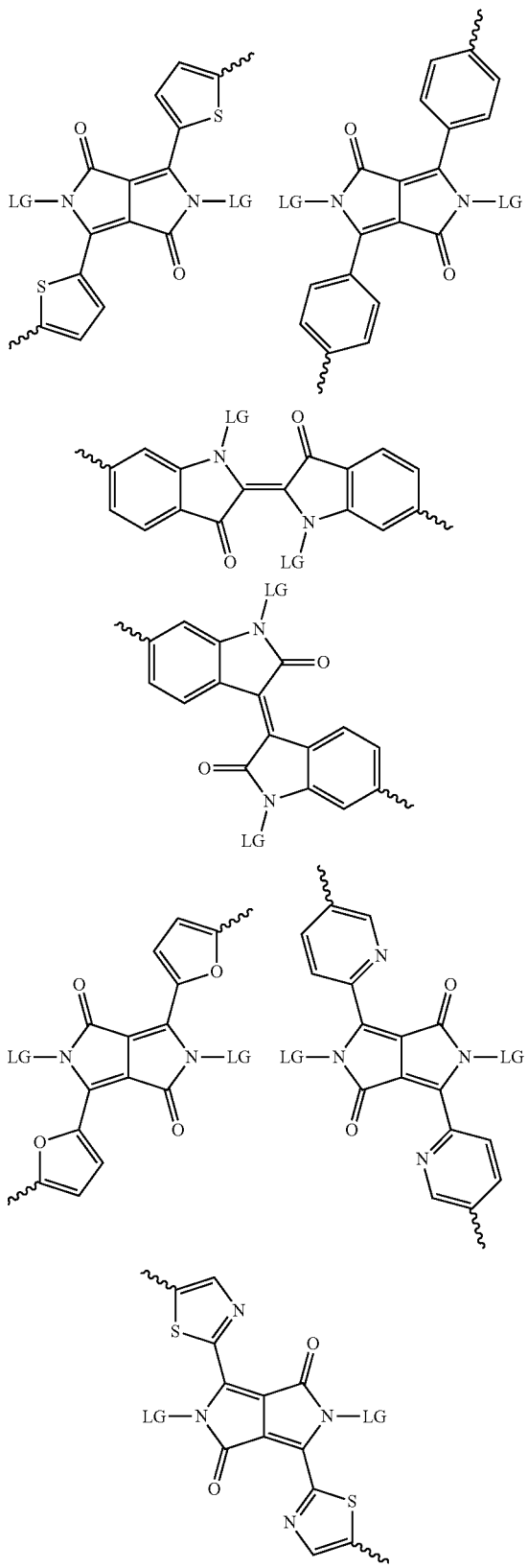

43
-continued
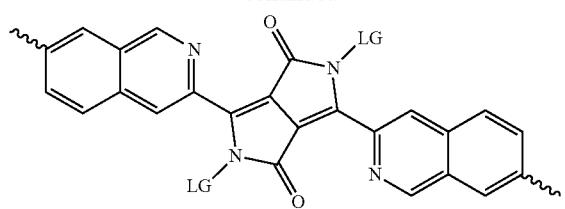
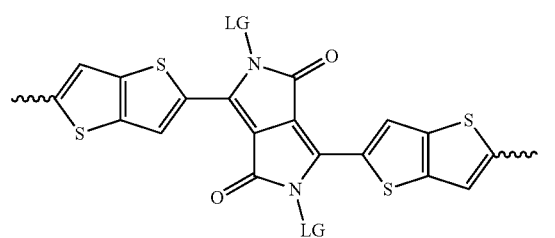
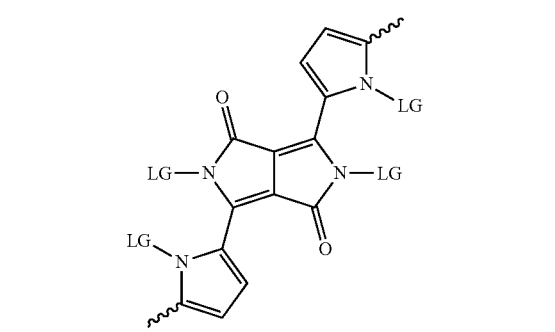
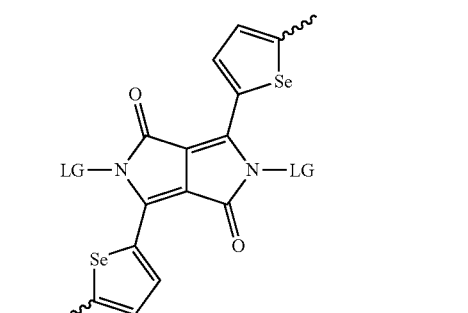
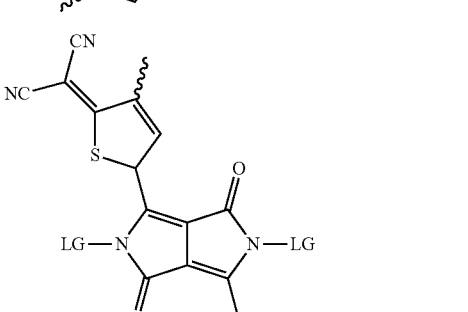
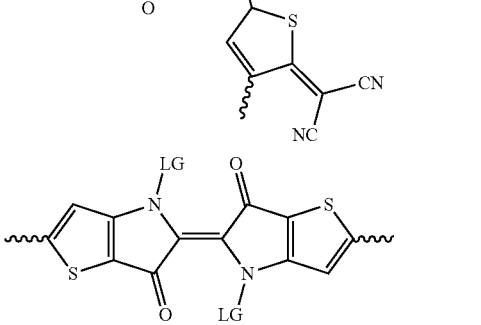
44
-continued
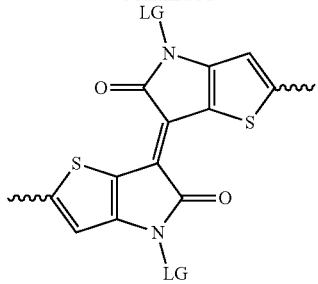
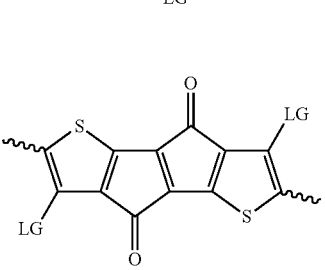
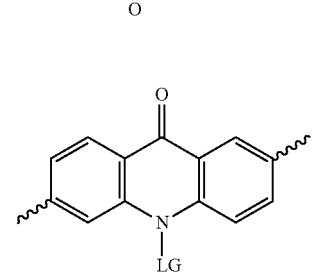
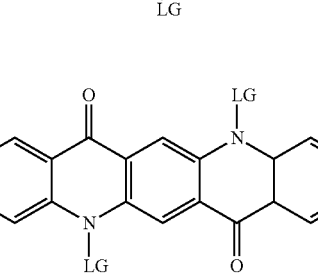
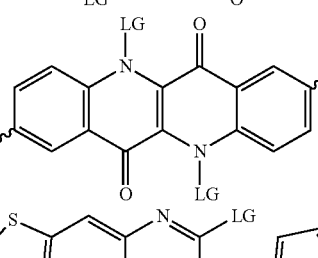
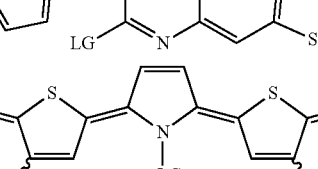
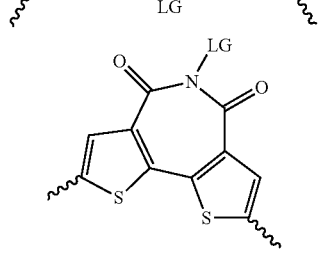

-continued
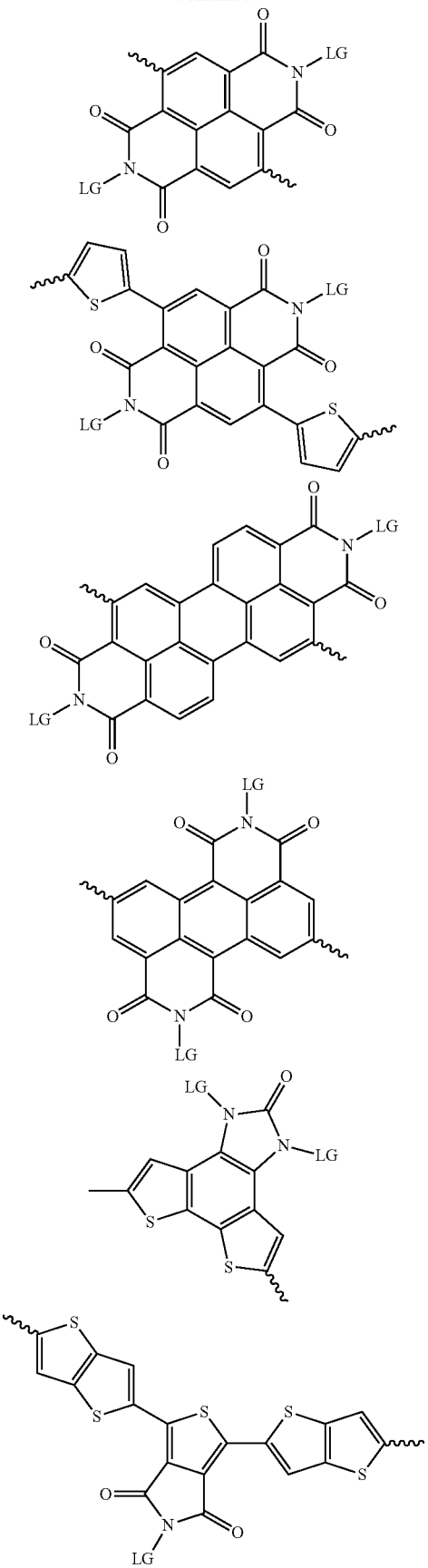
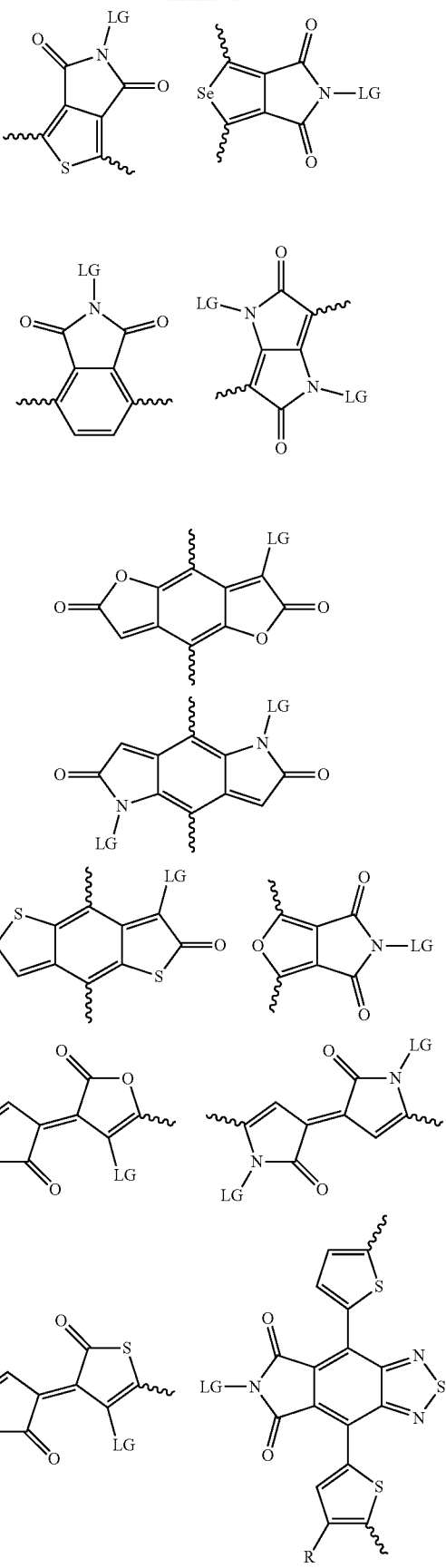

-continued
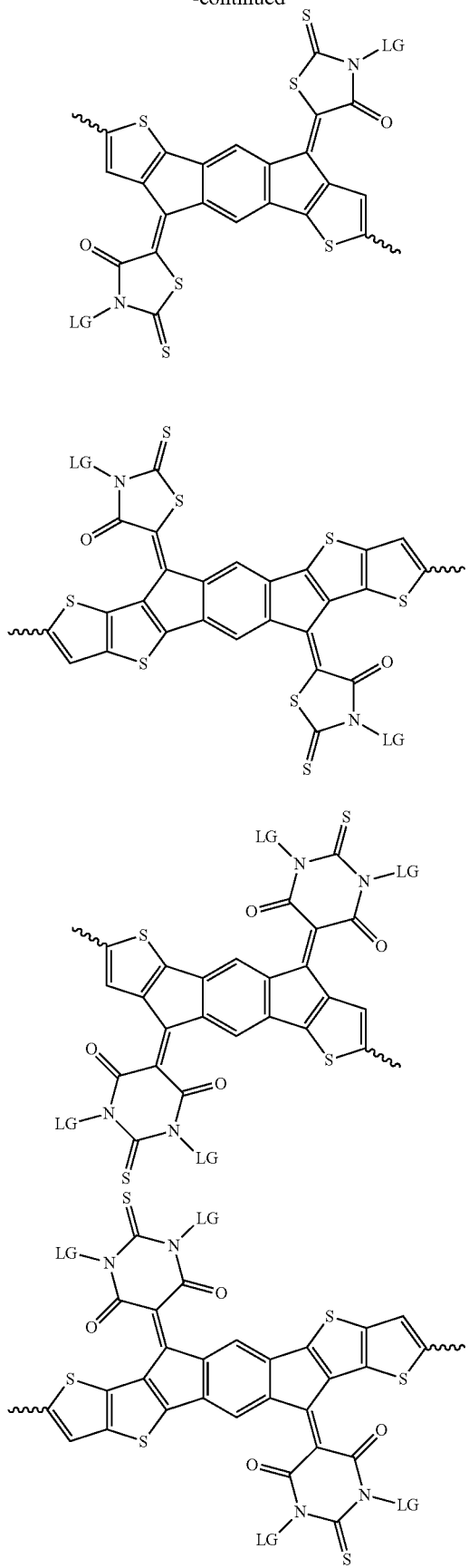
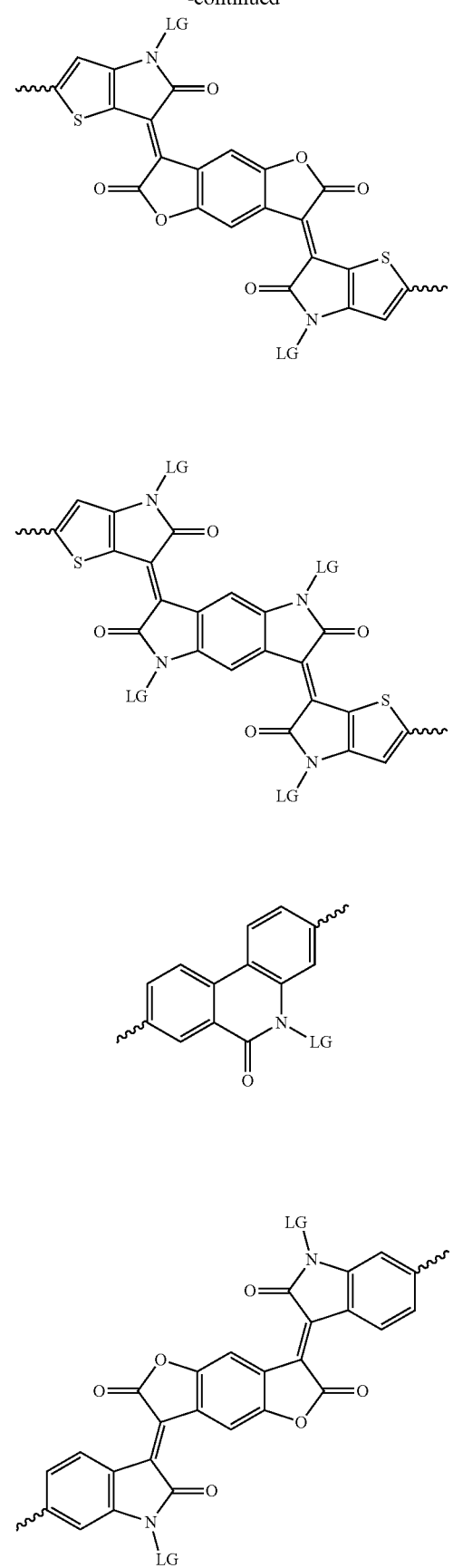

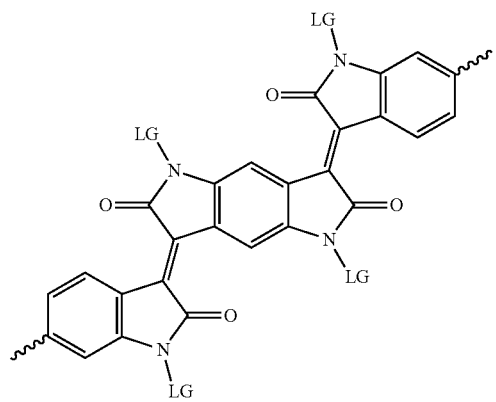

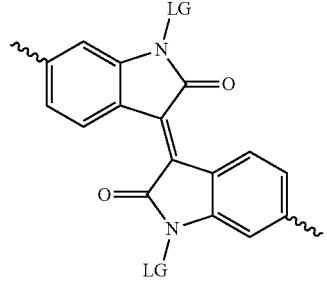

where LG represents leaving groups.

6. The method of claim 1, wherein the protecting group is selected from at least one of: tert-butoxycarbonyl (t-Boc), nitrobenzyl ester (NBE), ortho-nitrobenzyl (ONB), esters, ethers, xanthane, tetrahydropyranyl (THP), silyls, ketones, ketals, halogens, benzoins, coumarins, benzoquinolone, benzocoumarin, 7-nitroindoline, p-hydroxyphenacyl, or combinations thereof.

7. The method of claim 1, wherein the step of reacting comprises:

reacting at least one donor group with at least one protected acceptor group and at least one non-protected acceptor group to form a plurality of protecting group-containing crossbred OSC polymers.

8. The method of claim 7, wherein the at least one non-protected acceptor group is selected from at least one of: diketopyrrolopyrrole (DPP), indigo, isoindigo, or combinations thereof.

9. The method of claim 7, wherein the at least one non-protected acceptor group is selected from at least one of:

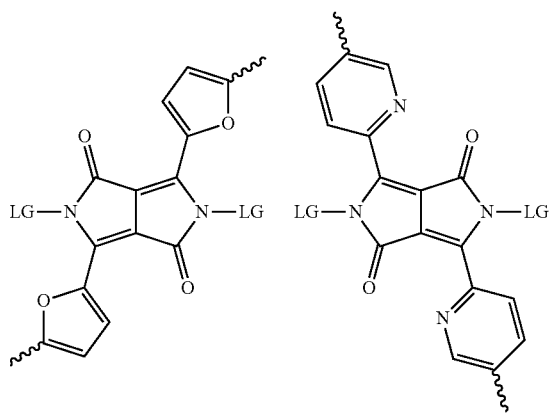

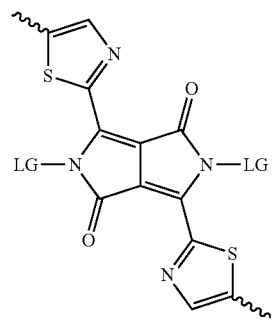

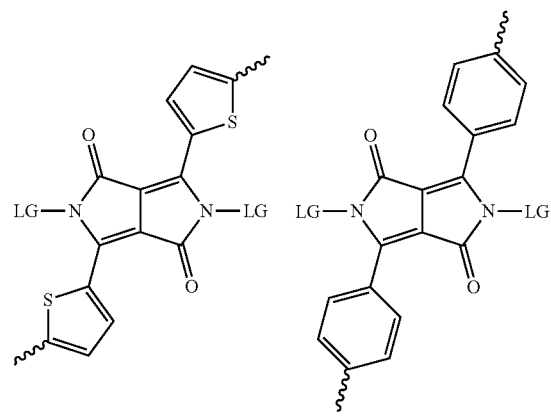

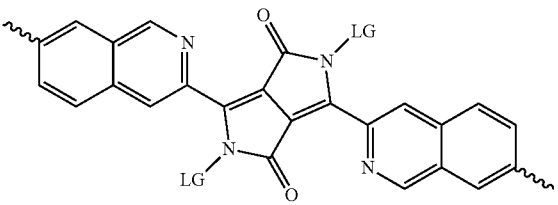

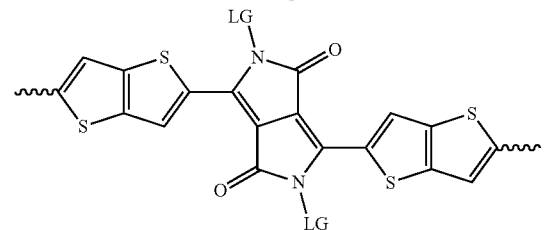

51
-continued
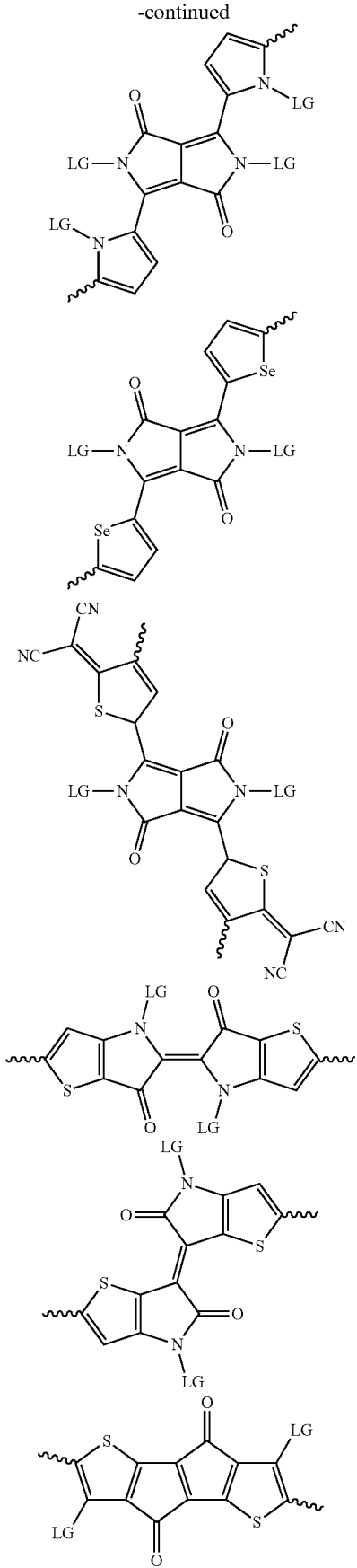
52
-continued
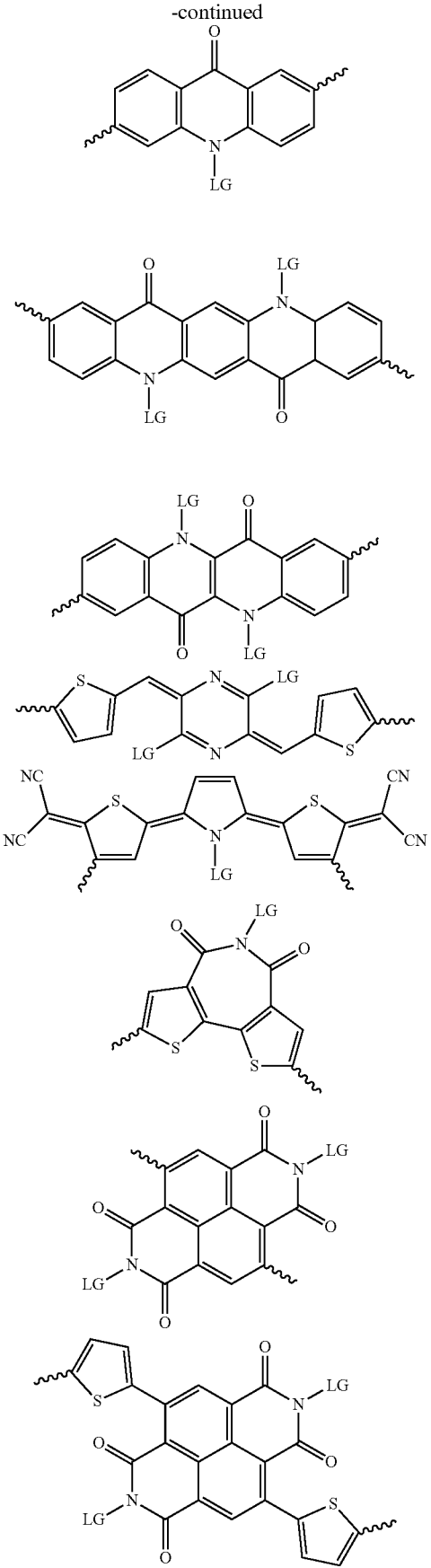

53
-continued
54
-continued
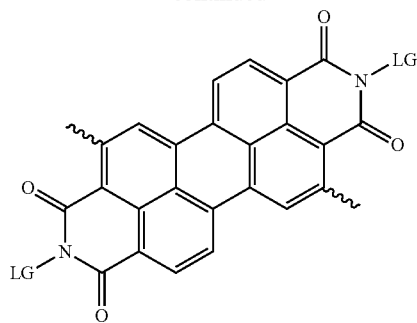
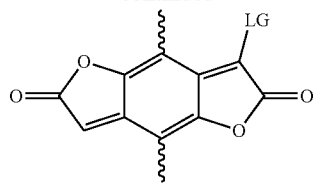
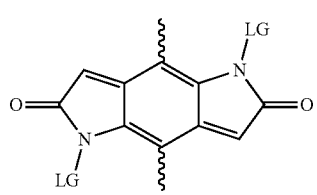
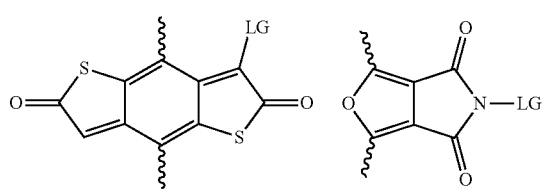
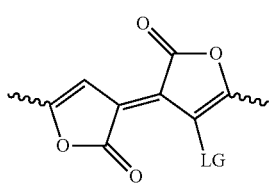
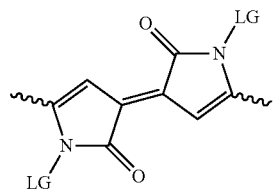
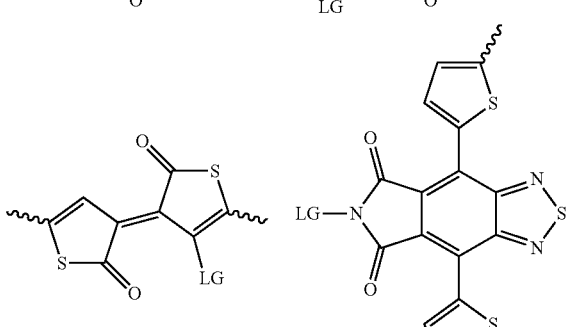
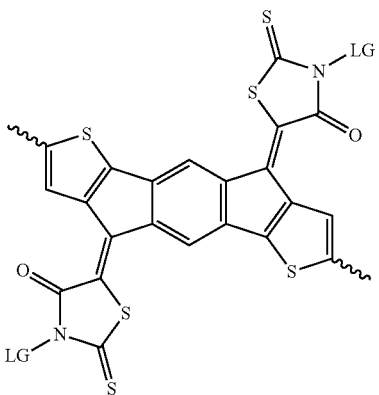

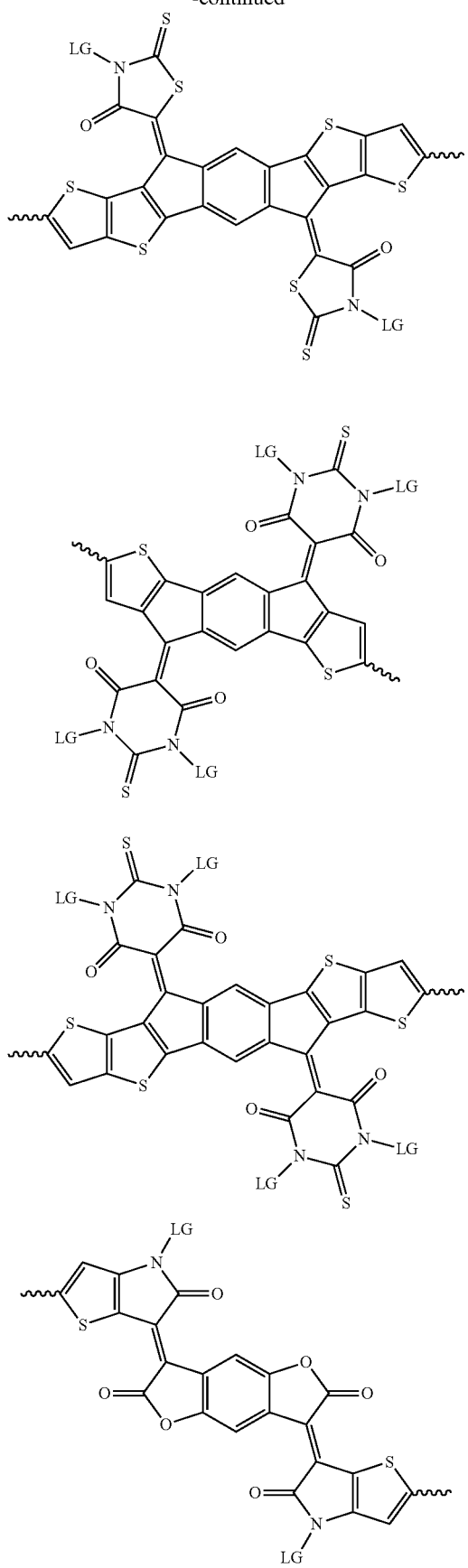
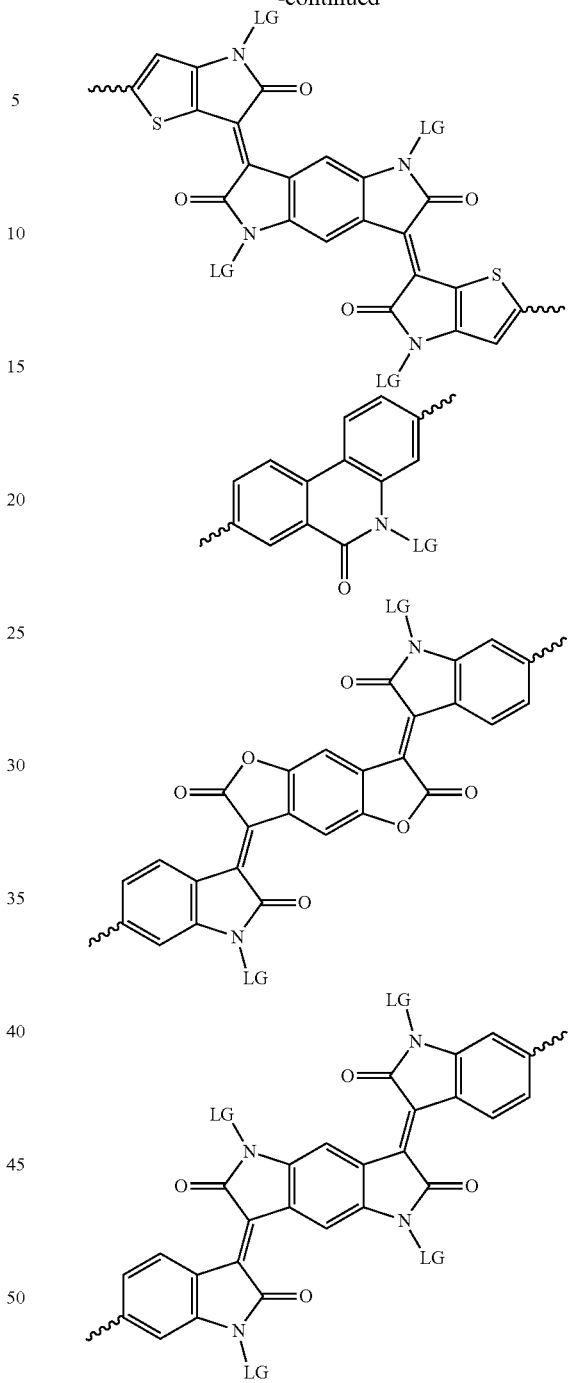

where LG represents leaving groups.

10. The method of claim 1, wherein the step of removing the protecting group comprises:
   dissolving the plurality of protecting group-containing OSC polymers in a solvent to form a mixture; and
   disposing the mixture onto a substrate to form a film.

11. The method of claim 10, wherein the step of removing the protecting group further comprises:
   thermal annealing the film at a temperature in a range of 100° C. to 500° C.

12. The method of claim 10, wherein the step of removing the protecting group further comprises:

exposing the film to UV light having an energy in a range of 10 mJ/cm² to 2000 mJ/cm².

13. The method of claim 12, wherein the UV light has an energy in a range of 400 mJ/cm² to 1600 mJ/cm².

14. An electronic device, comprising:
conjugated OSC polymers and configured to sense nitrogen-based gas at a detection level of 10 parts-per-billion (ppb), wherein the conjugated OSC polymers are synthesized by the method of claim 1.

15. The electronic device of claim 14, wherein the nitrogen-based gas comprises at least one of: ammonia ($NH_3$), nitric oxide (NO), triethylamine ($Et_3N$), piperidine (($CH_2$)$_5NH$), 1,4-diaminobutane ($NH_2(CH_2)_4NH_2$), or combinations thereof.

16. An electronic device, comprising:
conjugated OSC polymers and configured to sense gas, wherein the gas comprises at least one of: acetone, carbon monoxide (CO), hydrogen sulfide ($H_2S$), dichloromethane ($CH_2Cl_2$), ethanol ($CH_3CH_2OH$), ethyl acetate ($C_4H_8O_2$), hexane, hydrogen chloride (HCl), or combinations thereof, wherein the conjugated OSC polymers are synthesized using the method of claim 1.

17. The method of claim 1, wherein the at least one donor group is:

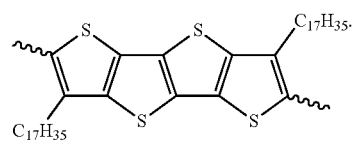

18. The method of claim 1, wherein the at least one protected acceptor group is:

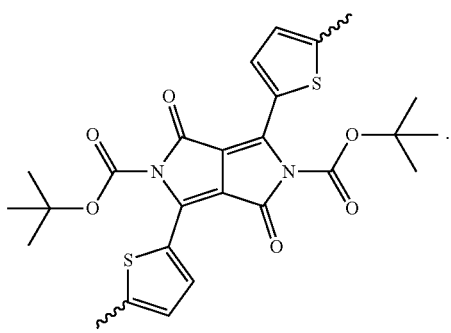

19. The method of claim 1, wherein the at least one donor group is:

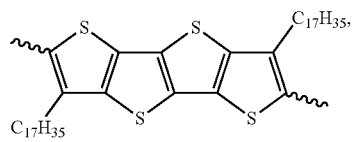

and the at least one protected acceptor group is:

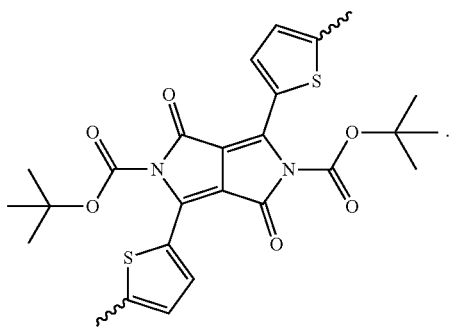

* * * * *

UNITED STATES PATENT AND TRADEMARK OFFICE
CERTIFICATE OF CORRECTION

| | | |
|---|---|---|
| PATENT NO. | : 12,227,613 B2 | Page 1 of 1 |
| APPLICATION NO. | : 17/495970 | |
| DATED | : February 18, 2025 | |
| INVENTOR(S) | : He et al. | |

It is certified that error appears in the above-identified patent and that said Letters Patent is hereby corrected as shown below:

In the Claims

Claim 5, Column 45, around Lines 45-55, delete:

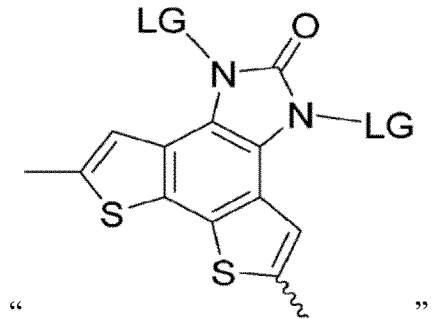

" "

And insert:

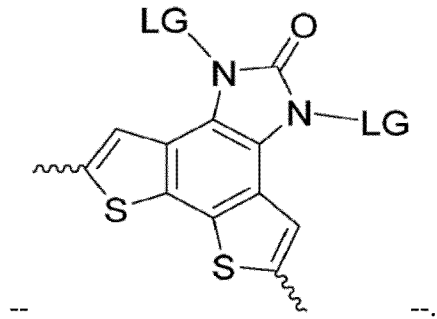

-- --.

Signed and Sealed this
Second Day of December, 2025

John A. Squires
*Director of the United States Patent and Trademark Office*